(12) United States Patent
Kalscheuer et al.

(10) Patent No.: US 7,118,896 B2
(45) Date of Patent: Oct. 10, 2006

(54) METHODS AND COMPOSITIONS FOR MODIFICATION OF LIPID BIOSYNTHESIS

(75) Inventors: Rainer Kalscheuer, Münster (DE); Alexander Steinbuchel, Altenberge (DE); Toni Voelker, Davis, CA (US)

(73) Assignee: Monsanto Technology, L.L.C., St. Louis, MO (US)

( * ) Notice: Subject to any disclaimer, the term of this patent is extended or adjusted under 35 U.S.C. 154(b) by 379 days.

(21) Appl. No.: 10/378,558

(22) Filed: Mar. 3, 2003

(65) Prior Publication Data

US 2004/0009576 A1 Jan. 15, 2004

Related U.S. Application Data

(60) Provisional application No. 60/360,774, filed on Mar. 1, 2002.

(51) Int. Cl.
| | |
|---|---|
| C12P 7/64 | (2006.01) |
| C12N 1/21 | (2006.01) |
| C12N 1/16 | (2006.01) |
| C12N 15/63 | (2006.01) |
| C12N 5/02 | (2006.01) |
| C07H 21/04 | (2006.01) |
| C12N 9/00 | (2006.01) |
| C12N 9/10 | (2006.01) |

(52) U.S. Cl. .................. 435/134; 435/183; 435/193; 435/252.3; 435/252.33; 435/252.34; 435/254.11; 435/320.1; 435/325; 435/410; 536/23.2

(58) Field of Classification Search ............... 435/193, 435/252.3, 254.11, 320.1, 325, 410, 134, 435/183, 252.33, 252.34; 536/23.2
See application file for complete search history.

(56) References Cited

U.S. PATENT DOCUMENTS 6,143,538 A   11/2000 Somerville et al. ......... 435/189
6,492,509 B1  12/2002 Lardizabal et al. ........ 536/23.6

FOREIGN PATENT DOCUMENTS

WO   WO 93/10241   5/1993

OTHER PUBLICATIONS

Barbe et al., "Unique features revealed by the genome sequence of acinetobacter sp. adp1, a versatile and naturally transformation competent bacterium," *Nucleic Acides Research*, 32:5766-5779, 2004.
Coleman et al., "Enzymes of triacylglycerol synthesis and their regulation," *Progress in Lipid Research*, 43:134-176, 2004.
EMBL Database XP-002336524.
Kalscheuer et al, "In vitro and invivo biosynthesis of wax diesters by an unspecific bifunctional wax ester synthase/acyl-coa:diacylglycerol acyltransferase from acinetobacter calcoaceticus adp1," *Eur. J. Lipid Sci Technol.I*, 105:578-584, 2003.
Kalscheuer et al., "A novel bifunctional wax ester synthase/acyl-coa:diacylglycerol acyltransferase mediates wax ester and triacylglycerol biosynthesis in acinetobacter calcoaceticus adp1," *J of Biological Chemistry*, 278, 8075-8082, 2003.
Kalscheuer et al., "Synthesis of novel lipids in saccharomyces cerevisiae by heterologous expression of an unspecific bacterial acyltransferase," *Applied and Environmental Microbiology*, 70:7119-7125, 2004.
Lardizabel et al., "Purification of a jojoba embryo wax synthase, cloning of its cdna, and production of high levels of wax in seeds of trangenic arabidopsis," *Plant Physiology*, 122:645-655, 2000.
Stoveken et al., "The was ester synthase/acyl coenzyme a:diacylglycerol acyltransferase from acinetobacter sp. strain adp1: characterization of a novel type of acyltransferase," *J Bacteriology*, 187:1369-1376, 2005.
Uthoff et al., "Thio wax ester biosynthesis utilizing the unspecific bifunctional wax ester synthase/acyl coenzyme a:diacylglycerol acyltransferase of acinetobacter sp. strain adp1," *Applied and Environmental Microbiology*, 71:790-796, 2005.
Alvarez et al., "Accumulation of storage lipids in species of Rhodococcus and Nocardia and effect of inhibitors and polyethylene glycol," *Fett/Lipid*, 9:239-246, 1997.
Cases et al., "Cloning of DGAT2, a second mammalian diacylglycerol acyltransferase, and related family members," *J. Biol. Chem.*, 276:38870-38876, 2001.
Chen and Farese, "DGAT and triglyceride synthesis: a new target for obesity treatment," *Trends Cardiovasc. Med.*, 10:188-192, 2000.
Cole et al., "Deciphering the biology of Mycobacterium tuberculosis from the complete genome sequence," *Nature*, 393:537-544, 1998.
Cole et al., "Deciphering the biology of Mycobacterium tuberculosis from the complete genome sequence," *Nature*, 396:190-198, 1998.
Dahlqvist et al., "Phospholipid: diacylglycerol acyltransferase : an enzyme that catalyzes the acyl-CoA-independent formation of triacylglycerol in yeast and plants," *Proc. Natl. Acad. Sci. USA*, 97:6487-6492, 2000.
Fixter et al., "Structure, distribution and function of wax esters in *Acinetobacter calcoaceticus*," *J. Gen. Microbiol.*, 132:3147-3157, 1986.
GenBank Accession No. AF149919.
Lehner and Kuksis, "Biosynthesis of triacylglycerols," *Prog. Lipid Res.*, 35:169-201, 1996.
Lehner and Kuksis, "Triacylglycerol synthesis by an sn-1,2(2,3)-diacylglycerol transacylase from rat intestinal microsomes," *J. Biol. Chem.*, 268:8781-8786, 1993.

(Continued)

*Primary Examiner*—Elizabeth Slobodyansky
(74) *Attorney, Agent, or Firm*—Fulbright & Jaworski L.L.P.

(57) ABSTRACT

The invention provides polypeptides having wax ester synthase and acyl-CoA:diacylglycerol acyltransferase activity. Also provided are the nucleic acids encoding such polypeptides, cells and organisms transformed therewith and methods of use thereof. The invention allows the modification of lipid profiles in host cells and organisms. Novel methods for the production of waxy esters are also provided by the invention.

21 Claims, 13 Drawing Sheets

OTHER PUBLICATIONS

Nakagawa et al., "Metabolism of triacylglycerol in *Mycobacterium smegmatis*," *J. Biochem.*, 80:923-928, 1976.

Olukoshi and Packter, "Importance of stored triacylglycerols in Streptomyces: possible carbon source for antibiotics," *Microbiology*, 140:931-943, 1994.

Reiser and Somerville, "Isolation of mutants of *Acinetobacter calcoaceticus* deficient in wax ester synthesis and complementation of one mutation with a gene encoding a fatty acyl coenzyme a reductase," *J. Bacteriol.*, 179:2969-2975, 1997.

Stachelhaus et al., "Peptide bond formation in nonribosomal peptide biosynthesis," *J. Biol. Chem.*, 273:22773-22781, 1998.

Steinbüchel, "Polyhydroxyalkanoic acids," *In Biomaterials*, Byrom, (Ed.), Chapter 3: 125-213, MacMillan, London, 1991.

Stobart et al., "Triacylglycerols and synthesised and utilized by transacylation reactions in microsomal preparations of developing safflower (*Carthamus tinctorius* L.) seeds," *Planta*, 203:58-66, 1997.

Wun et al., "Neutral lipid biosynthesis in *Mycobacterium smegmatis*," *Biochim. Biophys. Acta*, 488:454-463, 1977.

Kalscheuer and Steinbuchel, "A novel bifunctional wax ester synthase/acyl-CoA: diacylglycerol acyltransferase mediates wax ester and triacylglycerol biosynthesis in *Acinetobacter calcoaceticus* ADP1," *JBC Papers*, In press, published as Manuscript M210533200 on Dec. 26, 2002.

```
GAATTCTGGC CTACATGCAG GCAACTTAAA TAAATAATTT AAAAAAAACC ACTGTTATTG
CAGTGGTTTT TTTTATGTAC TCGCTATTCA GTATAATTCG TTAGATTTAT GTTGATTAAT
AACGATATAC TCAATACTCG GTTCTATAAT TCTAAAAACA TAGCTCATAA AGGGTTATTA
ATATCTTTGC AGTGAGGCAA TCCACGCTAT GCGCCCATTA CATCCGATTG ATTTTATATT
CCTGTCACTA GAAAAAAGAC AACAGCCTAT GCATGTAGGT GGTTTATTTT TGTTTCAGAT
TCCTGATAAC GCCCCAGACA CCTTTATTCA AGATCTGGTG AATGATATCC GGATATCAAA
ATCAATCCCT GTTCCACCAT TCAACAATAA ACTGAATGGG CTTTTTTGGG ATGAAGATGA
AGAGTTTGAT TTAGATCATC ATTTTCGTCA TATTGCACTG CCTCATCCTG GTCGTATTCG
TGAATTGCTT ATTTATATTT CACAAGAGCA CAGTACGCTG CTAGATCGGG CAAAGCCCTT
GTGGACCTGC AATATTATTG AAGGAATTGA AGGCAATCGT TTTGCCATGT ACTTCAAAAT
TCACCATGCG ATGGTCGATG GCGTTGCTGG TATGCGGTTA ATTGAAAAAT CACTCTCCCA
TGATGTAACA GAAAAAAGTA TCGTGCCACC TTGGTGTGTT GAGGGAAAAC GTGCAAAGCG
CTTAAGAGAA CCTAAAACAG GTAAAATTAA GAAATCATG TCTGGTATTA AGAGTCAGCT
TCAGGCGACA CCCACAGTCA TTCAAGAGCT TTCTCAGACA GTATTTAAAG ATATTGGACG
TAATCCTGAT CATGTTTCAA GCTTTCAGGC GCCTTGTTCT ATTTTGAATC AGCGTGTGAG
CTCATCGCGA CGTTTTGCAG CACAGTCTTT TGACCTAGAT CGTTTTCGTA ATATTGCCAA
ATCGTTGAAT GTGACCATTA ATGATGTTGT ACTAGCGGTA TGTTCTGGTG CATTACGTGC
GTATTTGATG AGTCATAATA GTTTGCCTTC AAAACCATTA ATTGCCATGG TTCCAGCCTC
TATTCGCAAT GACGATTCAG ATGTCAGCAA CCGTATTACG ATGATTCTGG CAAATTTGGC
AACCCACAAA GATGATCCTT TACAACGTCT TGAAATTATC CGCCGTAGTG TTCAAAACTC
AAAGCAACGC TTCAAACGTA TGACCAGCGA TCAGATTCTA AATTATAGTG CTGTCGTATA
TGGCCCTGCA GGACTCAACA TAATTTCTGG CATGATGCCA AAACGCCAAG CCTTCAATCT
GGTTATTTCC AATGTGCCTG GCCCAAGAGA GCCACTTTAC TGGAATGGTG CCAAACTTGA
TGCACTCTAC CCAGCTTCAA TTGTATTAGA CGGTCAAGCA TTGAATATTA CAATGACCAG
TTATTTAGAT AAACTTGAAG TTGGTTTGAT TGCATGCCGT AATGCATTGC CAAGAATGCA
GAATTTACTG ACACATTTAG AAGAAGAAAT TCAACTATTT GAAGGCGTAA TTGCAAAGCA
GGAAGATATT AAAACAGCCA ATTAAAAACA ATAAACTTGA TTTTTTAATT TATCAGATAA
AACTAAAGGG CTAAATTAGC CCTTTAGTTT TTAACAGTAC GACACTGTTT AAGTAATTGA
TGACACACAT GATGAACCAT TGCAGTCGTG ATCTGGATTT CTTTACCTTG ATCATTGACC
ATATAACAAG AATTGGCAGT TTTGTTATCA ACCATATGCG TTGAACCTTG AGCTAGTATT
CTTTCACTTA CATTCATGCG AGATACCCCG TTATTTGCTA AGACTAATAT GGGAGAAAAG
TCTTTGGCTA TGTTGTGTAC CTAGTATTGA AAATTCGGAT CC
```

Figure 5.

EcoRI      S/D

GAATTCAAGG AGGTATCCAC GCTATGCGCC CATTACATCC GATTGATTTT ATATTCCTGT
CACTAGAAAA AAGACAACAG CCTATGCATG TAGGTGGTTT ATTTTTGTTT CAGATTCCTG
ATAACGCCCC AGACACCTTT ATTCAAGATC TGGTGAATGA TATCCGGATA TCAAAATCAA
TCCCTGTTCC ACCATTCAAC AATAAACTGA ATGGGCTTTT TTGGGATGAA GATGAAGAGT
TTGATTTAGA TCATCATTTT CGTCATATTG CACTGCCTCA TCCTGGTCGT ATTCGTGAAT
TGCTTATTTA TATTTCACAA GAGCACAGTA CGCTGCTAGA TCGGGCAAAG CCCTTGTGGA
CCTGCAATAT TATTGAAGGA ATTGAAGGCA ATCGTTTGC CATGTACTTC AAAATTCACC
ATGCGATGGT CGATGGCGTT GCTGGTATGC GGTTAATTGA AAAATCACTC TCCCATGATG
TAACAGAAAA AAGTATCGTG CCACCTTGGT GTGTTGAGGG AAAACGTGCA AAGCGCTTAA
GAGAACCTAA AACAGGTAAA ATTAAGAAAA TCATGTCTGG TATTAAGAGT CAGCTTCAGG
CGACACCCAC AGTCATTCAA GAGCTTTCTC AGACAGTATT TAAAGATATT GGACGTAATC
CTGATCATGT TTCAAGCTTT CAGGCGCCTT GTTCTATTTT GAATCAGCGT GTGAGCTCAT
CGCGACGTTT TGCAGCACAG TCTTTTGACC TAGATCGTTT TCGTAATATT GCCAAATCGT
TGAATGTGAC CATTAATGAT GTTGTACTAG CGGTATGTTC TGGTGCATTA CGTGCGTATT
TGATGAGTCA TAATAGTTTG CCTTCAAAAC CATTAATTGC CATGGTTCCA GCCTCTATTC
GCAATGACGA TTCAGATGTC AGCAACCGTA TTACGATGAT TCTGGCAAAT TTGGCAACCC
ACAAAGATGA TCCTTTACAA CGTCTTGAAA TTATCCGCCG TAGTGTTCAA AACTCAAAGC
AACGCTTCAA ACGTATGACC AGCGATCAGA TTCTAAATTA TAGTGCTGTC GTATATGCC
CTGCAGGACT CAACATAATT TCTGGCATGA TGCCAAAACG CCAAGCCTTC AATCTGGTTA
TTTCCAATGT GCCTGGCCCA AGAGAGCCAC TTTACTGGAA TGGTGCCAAA CTTGATGCAC
TCTACCCAGC TTCAATTGTA TTAGACGGTC AAGCATTGAA TATTACAATG ACCAGTTATT
TAGATAAACT TGAAGTTGGT TTGATTGCAT GCCGTAATGC ATTGCCAAGA ATGCAGAATT
TACTGACACA TTTAGAAGAA GAAATTCAAC TATTTGAAGG CGTAATTGCA AAGCAGGAAG
ATATTAAAAC AGCCAATTAA AAACAATAAA CTTGATTTTT TAATTTATCA GATAAAACTA
AAGGGCTAAA TTAGCCCTGG ATCC
                      BamHI

Figure 6.

```
            AT GCGCCCATTA CATCCGATTG ATTTTATATT CCTGTCACTA GAAAAAAGAC
    AACAGCCTAT GCATGTAGGT GGTTTATTTT TGTTTCAGAT TCCTGATAAC GCCCCAGACA
    CCTTTATTCA AGATCTGGTG AATGATATCC GGATATCAAA ATCAATCCCT GTTCCACCAT
    TCAACAATAA ACTGAATGGG CTTTTTTGGG ATGAAGATGA AGAGTTTGAT TTAGATCATC
    ATTTTCGTCA TATTGCACTG CCTCATCCTG GTCGTATTCG TGAATTGCTT ATTTATATTT
    CACAAGAGCA CAGTACGCTG CTAGATCGGG CAAAGCCCTT GTGGACCTGC AATATTATTG
    AAGGAATTGA AGGCAATCGT TTTGCCATGT ACTTCAAAAT TCACCATGCG ATGGTCGATG
    GCGTTGCTGG TATGCGGTTA ATTGAAAAAT CACTCTCCCA TGATGTAACA GAAAAAAGTA
    TCGTGCCACC TTGGTGTGTT GAGGGAAAAC GTGCAAAGCG CTTAAGAGAA CCTAAAACAG
    GTAAAATTAA GAAAATCATG TCTGGTATTA AGAGTCAGCT TCAGGCGACA CCCACAGTCA
    TTCAAGAGCT TTCTCAGACA GTATTTAAAG ATATTGGACG TAATCCTGAT CATGTTTCAA
    GCTTTCAGGC GCCTTGTTCT ATTTTGAATC AGCGTGTGAG CTCATCGCGA CGTTTTGCAG
    CACAGTCTTT TGACCTAGAT CGTTTTCGTA ATATTGCCAA ATCGTTGAAT GTGACCATTA
    ATGATGTTGT ACTAGCGGTA TGTTCTGGTG CATTACGTGC GTATTTGATG AGTCATAATA
    GTTTGCCTTC AAAACCATTA ATTGCCATGG TTCCAGCCTC TATTCGCAAT GACGATTCAG
    ATGTCAGCAA CCGTATTACG ATGATTCTGG CAAATTTGGC AACCCACAAA GATGATCCTT
    TACAACGTCT TGAAATTATC CGCCGTAGTG TTCAAAACTC AAAGCAACGC TTCAAACGTA
    TGACCAGCGA TCAGATTCTA AATTATAGTG CTGTCGTATA TGGCCCTGCA GGACTCAACA
    TAATTTCTGG CATGATGCCA AAACGCCAAG CCTTCAATCT GGTTATTTCC AATGTGCCTG
    GCCCAAGAGA GCCACTTTAC TGGAATGGTG CCAAACTTGA TGCACTCTAC CCAGCTTCAA
    TTGTATTAGA CGGTCAAGCA TTGAATATTA CAATGACCAG TTATTTAGAT AAACTTGAAG
    TTGGTTTGAT TGCATGCCGT AATGCATTGC CAAGAATGCA GAATTTACTG ACACATTTAG
    AAGAAGAAAT TCAACTATTT GAAGGCGTAA TTGCAAAGCA GGAAGATATT AAAACAGCCA
    ATTAA
```

Figure 8.

```
MRPLHPIDFI  FLSLEKRQQP  MHVGGLFLFQ  IPDNAPDTFI  QDLVNDIRIS  KSIPVPPFNN
KLNGLFWDED  EEFDLDHHFR  HIALPHPGRI  RELLIYISQE  HSTLLDRAKP  LWTCNIIEGI
EGNRFAMYFK  IHHAMVDGVA  GMRLIEKSLS  HDVTEKSIVP  PWCVEGKRAK  RLREPKTGKI
KKIMSGIKSQ  LQATPTVIQE  LSQTVFKDIG  RNPDHVSSFQ  APCSILNQRV  SSSRRFAAQS
FDLDRFRNIA  KSLNVTINDV  VLAVCSGALR  AYLMSHNSLP  SKPLIAMVPA  SIRNDDSDVS
NRITMILANL  ATHKDDPLQR  LEIIRRSVQN  SKQRFKRMTS  DQILNYSAVV  YGPAGLNIIS
GMMPKRQAFN  LVISNVPGPR  EPLYWNGAKL  DALYPASIVL  DGQALNITMT  SYLDKLEVGL
IACRNALPRM  QNLLTHLEEE  IQLFEGVIAK  QEDIKTAN
```

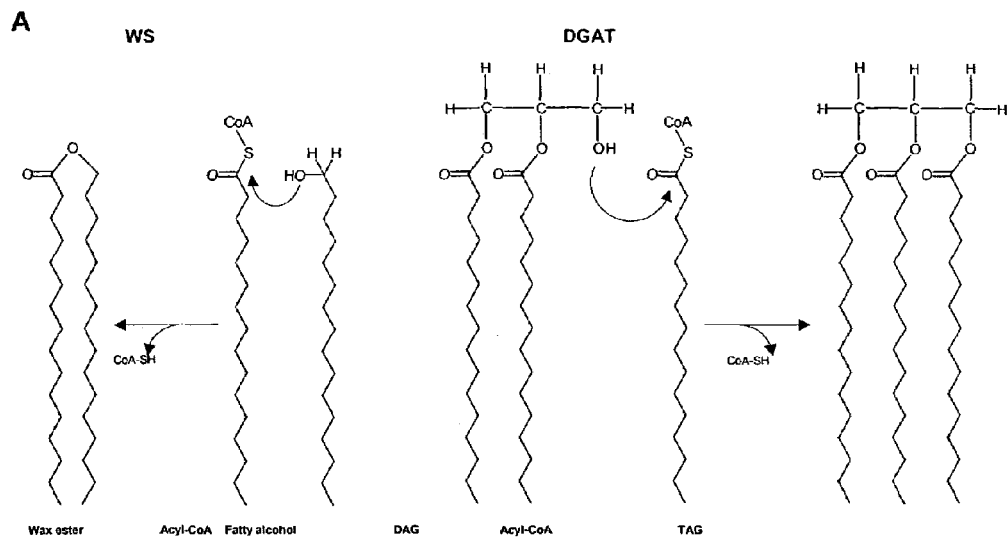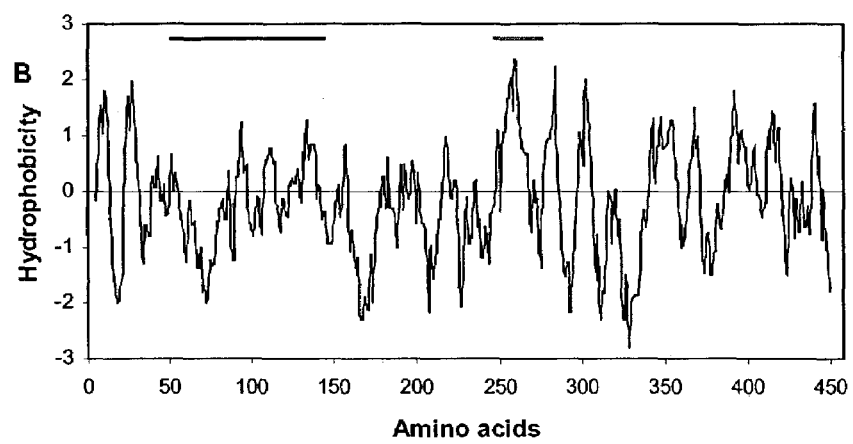
FIG. 12

METHODS AND COMPOSITIONS FOR MODIFICATION OF LIPID BIOSYNTHESIS

This application claims priority to U.S. Provisional Patent Application Ser. No. 60/360,774, filed on Mar. 1, 2002, the entire disclosure of which is specifically incorporated herein by reference.

BACKGROUND OF THE INVENTION

1. Field of the Invention

The invention relates generally to newly identified and isolated polynucleotides, proteins encoded by the polynucleotides, methods for producing proteins, and uses for the polynucleotides and proteins. More specifically, the current invention relates to bifunctional wax ester synthase proteins, polynucleotides encoding the proteins, and methods and compositions related thereto.

2. Description of Related Art

The capability for biosynthesis of neutral lipids is widely distributed in nature and is found in animals, plants as well as microorganisms. In bacteria, the most abundant class of neutral lipids are polyhydroxyalkanoic acids serving as intracellular carbon and energy storage (Steinbüchel, 1991), but also few examples of substantial triacylglycerol (TAG) accumulation have been reported for species mainly belonging to the actinomycetes genera *Mycobacterium* (Barksdale and Kim, 1977), *Nocardia* and *Rhodococcus* (Alvarez et al., 1997) and *Streptomyces* (Olukoshi and Packter, 1994). Furthermore, biosynthesis of wax esters (oxoesters of long-chain primary fatty alcohols and long-chain fatty acids) has been frequently reported for members of the genus *Acinetobacter* (Fixter et al., 1986).

TAGs are the dominating storage lipid in animals, plants and eukaryotic microorganisms. TAG biosynthesis is involved in animals in numerous processes such as regulation of plasma TAG concentration, fat storage in adipocytes and milk production (Bell and Coleman, 1980). In plants, TAG synthesis is mainly important for the generation of seed oils (Lassner, 1997) Using diacylglycerol (DAG) as a substrate, three different classes of enzymes are known mediating TAG formation (Lehner and Kuksis, 1996). Acyl-CoA: DAG acyltransferase (DGAT) catalyzes the acylation of DAG using acyl-CoA as a substrate. Two DGAT families designated as DGAT1 and DGAT2 are known, which exhibit no sequence homologies to each other. Members of the DGAT1 gene family occur in animals and plants (Cases et al., 1998; Hobbs et al., 1999; Routaboul et al., 1999; Zou et al., 1999), whereas members of the DGAT2 gene family were found in animals (Cases et al., 2001), plants (Bouvier-Navée et al., 2000) and yeasts (Oelkers et al., 2002). In human, one DGAT1 related gene and five DGAT2 related genes were identified (Cases et al., 2001).

Recently, DGAT has attracted great interest since it is a potential therapeutical target for obesity treatment (Chen and Farese Jr., 2000). Acyl-CoA-independent TAG synthesis is mediated by a phospholipid:DAG acyltransferase found in yeast and plants, which uses phospholipids as acyl donors for DAG esterification (Dahlqvist et al., 2000). A third alternative mechanism present in animals and plants is TAG synthesis by a DAG-DAG-transacylase which uses DAG as acyl donor and acceptor yielding TAG and monoacylglycerol (Lehner and Kuksis, 1993; Stobart et al., 1997), but no gene coding such a transacylase could be identified yet.

Linear wax esters are lipophilic compounds containing a long chain fatty alcohol esterified to a long chain fatty acid. These wax esters are found in a number of diverse organisms ranging from mammals to plants to bacteria. For instance, wax esters are the principal component of spermaceti oil which, until recently, was obtained from the head cavity of sperm whales. Since the world-wide ban on whale hunting, however, the only natural source of wax esters on a commercial scale has been the seeds of jojoba, a bush or shrub that is adapted to growth in hot arid habitats. In jojoba plants, waxes are stored in the seeds of the plant where they serve as a means of energy storage for developing seedlings. Wax esters have also been found in several species of bacteria such as *Acinetobacter calcoaceticus*, a gram negative aerobic bacteria that accumulates wax esters when grown under nitrogen limited conditions. Wax esters from these bacterial sources, however, have not been utilized on a commercial scale.

Wax esters have a multitude of important commercial applications in a variety of technical areas, including the medical, cosmetics and food industries as well as their more traditional usage as lubricants for mechanical parts and the like. The wax esters obtained from jojoba can replace sperm whale oil in most or all traditional uses. They are useful for applications in cosmetics, as a lubricant, as an additive for leather processing, as a carrier for pharmaceuticals and as a solvent. Hydrogenation of the wax to eliminate double bonds produces a hard wax which is useful for surface treatments, in textile sizing, in coating paper containers and in cosmetics (e.g., lipstick and creams). Sulphurization of the wax or other modifications make the substance useful in specialty lubricant applications, as a textile softener, as a component of printing inks, and as a component in many technical products such as corrosion inhibitors, surfactants, detergents, disinfectants, plasticizers, resins and emulsifiers. For some of these applications the fatty alcohol derived by hydrolysis of the wax ester is the most valuable ingredient derived from the wax ester.

Because the yield of the jojoba plant is extremely low, however, the oil is relatively expensive compared with edible oils from plants or technically comparable materials from petroleum and its use has been limited to cosmetic products. Thus, a need exists to develop an alternate biological source of wax esters. One possibility, in this respect, is to recombinantly engineer a microbial species for efficient production of wax esters. Toward that end, information concerning enzymes and enzymatic pathways which are involved in wax ester biosynthesis, and the nucleic acid sequences that encode these enzymes are needed.

The most detailed information concerning wax ester biosynthesis concerns wax biosynthesis in jojoba plants, where it appears that two enzymes catalyze the formation of wax esters. The first step of the pathway is catalyzed by a fatty acyl-CoA reductase which reduces very long chain fatty acyl CoA (a very long chain fatty acyl CoA generally having greater than 18 carbons), and is known to catalyze the formation of a long chain alcohol directly from this substrate via an aldehyde intermediate. The second enzyme (wax ester synthase), an acyl-CoA-fatty alcohol transferase catalyzes the formation of an ester linkage between acyl-CoA and a fatty alcohol to yield a wax ester.

The pathway of wax ester biosynthesis in *A. calcoaceticus*, in contrast to the jojoba plant, comprises three enzymatic steps involved in the conversion of long-chain acyl-CoA to wax esters. In the first step, acyl-CoA is reduced by an NADPH-dependent acyl-CoA reductase to the corresponding fatty aldehyde. In the second step, the aldehyde is further reduced to the corresponding fatty alcohol catalyzed by the fatty aldehyde reductase. Finally, an acyl-CoA:fatty alcohol acyl transferase (wax ester synthase) condenses the fatty alcohol with acyl-CoA resulting in the formation of the wax ester.

Wax ester synthesis and WS activity have been reported for *M. tuberculosis* (Wang et al., 1972), and TAG accumulation and DGAT activity have been shown for *M. smegmatis* (Nakagawa et al., 1976; Wun et al., 1977). However, no proteins or genes have been reported to which these activities could be attributed.

Irrespective of the species involved, therefore, a key enzymatic step involved in wax ester biosynthesis is the transfer of an acyl chain from fatty acyl-CoA to a fatty alcohol, and this reaction is catalyzed by wax ester synthase. While several wax ester synthases have been described in terms of their substrate specificities and intracellular locations, very little is known about the proteins associated with this activity and the genes encoding this enzyme. In fact, the only gene encoding a wax ester synthase that has been identified is from jojoba. Thus, a need exists to identify genes encoding wax ester synthases from other species. In particular, a need exists to identify genes encoding wax ester synthases from a species that could be engineered to produce wax esters in large quantities and at a relatively affordable cost. The present invention addresses this need by providing polynucleotide sequences encoding bacterial wax ester synthases.

SUMMARY OF THE INVENTION

In one aspect, the invention provides an isolated polynucleotide encoding a polypeptide having wax ester synthase/DGAT activity and having a nucleotide sequence at least about 60% homologous to SEQ ID NO:1. In certain embodiments of the invention, an isolated polynucleotide in accordance with the invention comprises a polynucleotide that hybridizes to SEQ ID NO:1 under conditions of 5×SSC, 50% formamide and 42° C., and which encodes a protein having the same biological function. Such polynucleotides may encode the same polypeptide as SEQ ID NO:1.

In another aspect of the invention provides a recombinant vector comprising a polynucleotide of the invention. In certain embodiments, the recombinant vector may comprise the polynucleotide linked to one or more regulatory regions and/or any other desired elements.

In yet another aspect, the invention provides a protein or polypeptide fragment encoded by the polynucleotide of SEQ ID NO:1 or a fragment thereof having wax ester synthase/ DGAT activity. In certain embodiments of the invention, a protein comprising the amino acid sequence of SEQ ID NO:4 or a fragment of SEQ ID NO:4 is provided, wherein said fragment has wax ester synthase activity. In certain embodiments of the invention, the protein and/or fragment may have wax ester synthase and DGAT activity. In certain further embodiments of the invention, a protein or polypeptide may comprise one or more of the following amino acid sequences: HHAXVDGV (SEQ ID NO:16), NDVVLA (SEQ ID NO:17), GALRXYL (SEQ ID NO:18), PLXAMVP (SEQ ID NO:19), ISNVPGP (SEQ ID NO:20), REPLYXNGA (SEQ ID NO:21), including one, two, three, four, five or all six of these amino acid sequences.

In still yet another aspect of the invention, a recombinant construct is provided comprising a polynucleotide sequence encoding a conserved polypeptide fragment with wax ester synthase and/or DGAT activity, and further wherein the polypeptide comprises at least one of the following amino acid sequences selected from the group consisting of HHAXVDGV (SEQ ID NO:16), NDVVLA (SEQ ID NO:17), GALRXYL (SEQ ID NO:18), PLXAMVP (SEQ ID NO:19), ISNVPGP (SEQ ID NO:20), REPLYXNGA (SEQ ID NO:21), including one, two, three, four, five or all six of these amino acid sequences. In one embodiment of the invention, the polynucleotide sequence is a bacterial sequence. In still yet another embodiment is provided a host cell containing this recombinant construct. In one embodiment of the invention, the host cell may be any type of cell.

In still yet another aspect, a method is provided a method for producing a wax ester comprising culturing a host cell described above under conditions permitting expression of the polypeptide having wax ester synthase activity. In certain embodiments of the invention, the polypeptide may have DGAT activity. The method may comprise culturing the cell in one or more substrates for the waxy ester synthase/DGAT. The wax ester may or may not be isolated from the host cell or any media in which the host cell is cultured.

In still yet another aspect, the invention provides a method of modifying accumulation of wax esters in a host cell that comprises transforming a host cell with a recombinant construct of the invention. In certain embodiments, the recombinant construct may comprise a regulatory sequence operably linked to a nucleic acid sequence, said nucleic acid sequence encoding a polynucleotide encoding a polypeptide having wax ester synthase and/or DGAT activity or a fragment thereof, and culturing said host cell under conditions wherein said host cell expresses a polypeptide having wax ester synthase and/or DGAT activity such that said host cell has a modified wax ester composition compared to host cells without the recombinant construct. In certain embodiments of the invention, the method comprises increasing the wax ester content of a host cell.

BRIEF DESCRIPTION OF THE DRAWINGS

These and other features, aspects, and advantages of the present invention will become better understood with regard to the following description, appended claims, and accompanying figures, where:

FIG. 5 is the nucleotide sequence of the PCR™-amplified 1.9-kbp fragment from *A. calcoaceticus* BD413 comprising the wax/dgat gene (SEQ ID NO:3). The wax gene is shown in bold face. A putative ribosome binding site is double-underlined. The EcoRI and BamHI restriction sites used for cloning are underlined.

FIG. 6 is the nucleotide sequence of the PCR™-amplified 1.47-kbp wax/dgat gene from *A. calcoaceticus* BD413 (SEQ ID NO:2). The wax gene is shown in bold face. The linked ribosome binding site (Shine/Dalgarno sequence) for *E. coli* is double-underlined. The EcoRI and BamHI restriction sites used for cloning are underlined.

FIG. 8 depicts the polynucleotide sequence of SEQ ID NO:1.

FIG. 9 depicts the deduced amino acid sequence of SEQ ID NO:4.

FIG. 10 shows an alignment of the polypeptide sequence encoded by SEQ ID NO:1 versus deduced bacterial sequences (SEQ ID NOs:24–31). Conserved regions are shown by shading.

FIGS. 12A, B shows properties of the bifunctional WS/DGAT. (FIG. 12A) Reactions catalyzed by the bifunctional enzyme. (FIG. 12B) Hydrophobicity plot (Kyte and Doolittle, 1982) of WS/DGAT (window size 9). A putative transmembrane domain predicted by the TMAP program is indicated by the grey bar. The black bar region exhibits some homology to a conserved condensing domain containing a putative active site.

(FIG. 13A) Fatty alcohol specificity of the WS reaction.

DETAILED DESCRIPTION OF THE INVENTION

Figure 1:
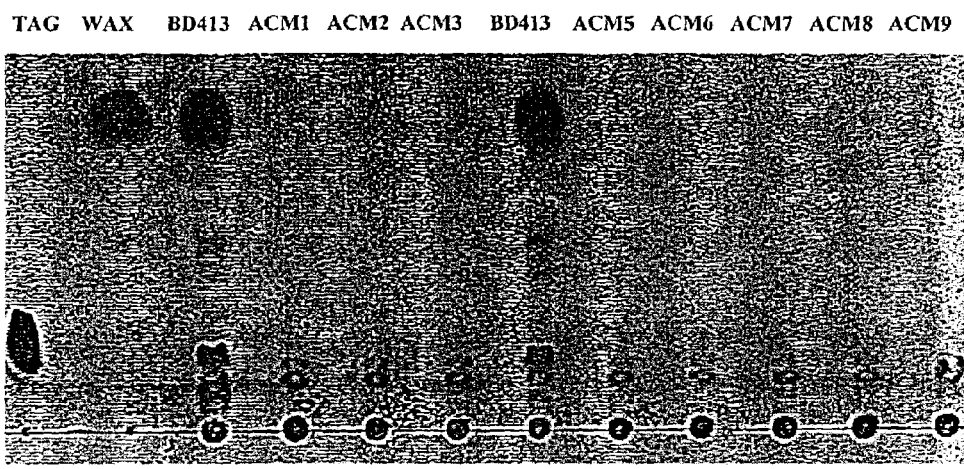
FIG. 1 shows the results of a thin layer chromatography ("TLC") analysis of miniTn10Km-induced mutants from *A. calcoaceticus* BD413 (Ndx$^r$) after cultivation under storage conditions. TAG, triolein standard; WAX, cetylpalmitate standard.

The present invention relates to the initial discovery and isolation of the polynucleotide encoding a wax ester synthase (WS) protein from *A. calcoaceticus*, which protein also has acyl-CoA:diacylglycerol acyltransferase (DGAT) activity (e.g., WS/DGAT). Therefore, when wax ester synthase polypepetides and nucleic acids are referred to herein this specifically includes the inherent bifunctional DGAT activity. The sequence from *A. calcoaceticus* has been determined and is given in SEQ ID NO:1 and is also set forth in FIG. 8. Moreover, the amino acid sequence of the wax ester synthase/DGAT protein produced by the isolated nucleic acid sequence has been deduced and is given in FIG. 9 and corresponds to SEQ ID NO:4. Although a particular embodiment of the nucleotide sequence disclosed herein is given in SEQ ID NO:1, it should be understood that other biologically functional equivalent forms of the nucleic acid sequence of the present invention can be readily isolated using conventional DNA-DNA and DNA-RNA hybridization techniques. Thus the present invention also includes nucleotide sequences that hybridize to SEQ ID NO:1 or its complement under moderate to high stringency conditions and encode proteins exhibiting the same or similar biological activity as that of protein of SEQ ID NO:4 disclosed herein. Also included in the invention are polynucleotides that exhibit 90%, preferably 92%, more preferably 95% and more 98% sequence identity with SEQ ID NO:1, its complement or SEQ ID NO:2.

One advance of the current invention relates to novel methods for the production of wax esters. A strong demand exists for large-scale production of cheap jojoba-like wax esters which have multiple commercial uses. Jojoba oil is the only alternative natural source of wax esters to sperm whale oil which is used at a commercial scale, but the high production costs restrict its use currently on cosmetical applications. The jojoba WS is not functionally expressed in microorganisms like *E. coli* and *S. cerevisiae*. In contrast, the inventors have demonstrated WS/DGAT that is active in different bacterial hosts. In *P. citronellolis*, the heterologous expression of WS/DGAT lead to production of wax esters if a long-chain fatty alcohol was provided as carbon source which also delivers fatty acyl-CoA during catabolism by the alkane degradation pathway. By variation of the fatty alcohol used as carbon source, one may vary the composition of the produced wax esters. The invention provides the basis, for example, for microbial biotechnological production of jojoba-like wax esters. The fast growth rates, the possibility to influence the wax composition by altering the culture conditions and the easy accessibility of bacteria to genetic and metabolic engineering will support such efforts.

In certain embodiments, the invention provides nucleic acid sequences that hybridize to SEQ ID NO:1 or its complement under moderate to high stringency conditions. As is well known in the art, stringency is related to the Tm of the hybrid formed. The Tm (melting temperature) of a nucleic acid hybrid is the temperature at which 50% of the bases are base-paired. For example, if one of the partners in a hybrid is a short oligonucleotide of approximately 20bases, 50% of the duplexes are typically strand separated at the $T_m$. In this case, the $T_m$ reflects a time-independent equilibrium that depends on the concentration of oligonucleotide. In contrast, if both strands are longer, the $T_m$ corresponds to a situation in which the strands are held together in structure possibly containing alternating duplex and denatured regions. In this case, the $T_m$ reflects an intramolecular equilibrium that is independent of time and polynucleotide concentration.

As is also well known in the art, $T_m$ is dependent on the composition of the polynucleotide (e.g. length, type of duplex, base composition, and extent of precise base pairing) and the composition of the solvent (e.g. salt concentration and the presence of denaturants such formamide). An equation for the calculation of $T_m$ can be found in Sambrook, et al. (2001), and is: $T_m = 81.5° C. - 16.6(\log_{10}[Na^+]) = 0.41(\% G+C) - 0.63(\% \text{ formamide}) - 600/L)$. Where L is the length of the hybrid in base pairs, the concentration of $Na^+$ is in the range of 0.01M to 0.4M and the G+C content is in the range of 30% to 75%. Equations for hybrids involving RNA can be found in the same reference. Alternative equations can be found in Davis et al. (1994).

Methods for hybridization and washing are well known in the art and can be found in standard references in molecular biology such as those cited herein. In general, hybridizations are usually carried out in solutions of high ionic strength (6×SSC or 6×SSPE) at a temperature 20–25' C. below the $T_m$. High stringency wash conditions are often determined empirically in preliminary experiments, but usually involve a combination of salt and temperature that is approximately 12–20° C. below the $T_m$. One example of such wash conditions is 5×SSC, 50% formamide at 42° C. An example with higher stringency conditions is 1×SSC at 60° C. Another example of high stringency wash conditions is 0.1×SSPE, 0.1% SDS at 42° C. (Meinkoth and Wahl, 1984). An example of even higher stringency wash conditions is 0.1×SSPE, 0.1% SDS at 50–65° C. In one preferred embodiment, high stringency washing is carried out under conditions of 1×SSC and 60° C.

It is well known to those of ordinary skill in the art that different compositions can result in equal stringency conditions for hybridization depending on well known factors such as the concentration of $Na^+$, the % formamide, the temperature, the $T_m$ of the hybrid to be formed, and the composition of the hybrid, e.g. DNA-DNA, DNA-RNA, or RNA-RNA. Thus the invention also encompasses nucleotide sequences that hybridize under conditions equivalent to those described above.

Also included in the invention are polynucleotides that exhibit 90%, preferably 92%, more preferably 95%, and still more preferably 98% sequence identity or homology with SEQ ID NO:1, its respective complement or SEQ ID NO:2. Such nucleotide sequences preferably hybridize to the nucleic acid of SEQ ID NO:1 or its respective complement under high stringency conditions.

"Homology," as is well understood in the art, is a relationship between two or more polypeptide sequences or two or more polynucleotide sequences, as determined by comparing the sequences. In the art, "homology" also means the degree of sequence relatedness between polypeptide or polynucleotide sequences, as determined by the match between strings of such sequences. "Homology" can be readily calculated by known methods including, but not limited to, those described in *Computational Molecular Biology* (1988); *Biocomputing. Informatics and Genome Projects* (1993); *Computer Analysis of Sequence Data, Part I* (1994); *Sequence Analysis in Molecular Biology* (1987); *Sequence Analysis Prime* (1991); and Carillo and Lipman (1988). Methods to determine homology are designed to give the largest match between the sequences tested. Moreover, methods to determine homology are codified in publicly available programs. Computer programs which can be used to determine identity/homology between two sequences include, but are not limited to, GCG (Devereux et al., 1984; suite of five BLAST programs, three designed for nucleotide sequences queries (BLASTN, BLASTX, and TBLASTX) and two designed for protein sequence queries (BLASTP and TBLASTN) (Coulson, 1994; Birren, et al., 1997). The BLAST X program is publicly available from NCBI and other sources (*BLAST Manual*; Altschul et al., 1990). The well known Smith Waterman algorithm can also be used to determine homology.

The present invention also involves recombinant polynucleotides comprising the isolated protein along with other sequences. Such recombinant polynucleotides are commonly used as cloning or expression vectors although other uses are possible. A recombinant polynucleotide is one in which polynucleotide sequences of different organisms have been joined together to form a single unit. A cloning vector is a self replicating DNA molecule that serves to transfer a DNA segment into a host cell. The three most common types of cloning vectors are bacterial plasmids, phages, and other viruses. An expression vector is a cloning vector designed so that a coding sequence inserted at a particular site will be transcribed and translated into a protein.

Both cloning and expression vectors contain nucleotide sequences that allow the vectors to replicate in one or more suitable host cells. In cloning vectors, this sequence is generally one that-enables the vector to replicate independently of the host cell chromosomes, and also includes either origins of replication or autonomously replicating sequences. Various bacterial and viral origins of replication are well known to those skilled in the art and include, but are not limited to the pBR322 plasmid origin, the 2 plasmid origin, and the SV40, polyoma, adenovirus, VSV and BPV viral origins.

The polynucleotide sequence of the present invention may be used to produce proteins by the use of recombinant expression vectors containing the sequence. A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papoviruses such as SV40, vaccinia viruses, adenoviruses, fowl pox viruses; pseudorabies viruses and retroviruses, and vectors derived from combinations thereof, such as those derived from plasmid and bacteriophage genetic elements, such as cosmids and phagemids. All such vectors may be used for expression in accordance with this aspect of the present invention. Generally, any vector suitable to maintain, propagate or express polynucleotides to express a polypeptide in a host may be used for expression in this regard. Therefore, any other vector that is replicable and viable in the host may be used.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4-:DNA ligase. Procedures for restriction and ligation that can be used to this end are well known and routine to those of skill in the art. Suitable procedures in this regard, and for constructing expression vectors using alternative techniques, which also are well known and routine to those-of skill in the art, are set forth in great detail in Sambrook et al., (2001); Ausubel et al. (1995).

In an expression vector, the sequence of interest is operably linked to a suitable regulatory sequence, expression control sequence or promoter recognized by the host cell to direct mRNA synthesis. Promoters are untranslated sequences located generally 100 to 1000 base pairs (bp) upstream from the start codon of a structural gene that regulate the transcription and translation of nucleic acid sequences under their control. Promoters are generally classified as either inducible or constitutive. Inducible promoters are promoters that initiate increased levels of transcription from DNA under their control in response to some change in the environment, e.g. the presence or absence of a nutrient or a change in temperature. Constitutive promoters, in contrast, maintain a relatively constant level of transcription. In addition, useful promoters can also confer appropriate cellular and temporal specificity. Such promoters include those that are developmentally-regulated or organelle, tissue or cell-specific.

A nucleic acid sequence is operably linked when it is placed into a functional relationship with another nucleic acid sequence. For example, DNA for a presequence or secretory leader is operatively linked to DNA for a polypeptide if it is expressed as a preprotein which participates in the secretion of the polypeptide; a promoter is operably linked to a coding sequence if it affects the transcription of the sequence; or a ribosome binding site is operably linked to a coding sequence if it is positioned so as to facilitate translation. Generally, operably linked sequences are contiguous and, in the case of a secretory leader, contiguous and in reading frame. Linking is achieved by blunt end ligation or ligation at restriction enzyme sites. If suitable restriction sites are not available, then synthetic oligonucleotide adapters or linkers can be used as is known to those skilled in the art (Sambrook et al., 2001; Ausubel et al., 1995).

Those skilled in the art will recognize that there are a number of promoters which are functional in bacterial cells, and have been described in the literature including constitutive, inducible, developmentally regulated, and environmentally regulated promoters. Of particular interest is the use of promoters (also referred to as transcriptional initiation regions) functional in bacterial host cells. Representatives of such promoters include the phage lambda PL promoter, the *E. coli* lac, trp and tac promoters, the SV40 early and late promoters, promoters of retroviral LTRs, the CaMV 35S promoter (Assaad and Signer, 1990), coconut foliar decay virus (CFDV) DNA (U.S. Pat. No. 6,303,345), and the endogenous promoters of *P. citronellolis*, to name just a few of the well-known promoters. It will be understood that numerous promoters not mentioned are suitable for use in this aspect of the invention, are well known, and may be readily employed by those of skill in the manner illustrated by the discussion and the examples herein. Other promoters known to control the expression of genes in prokaryotic or eukaryotic cells can be used and are known to those skilled in the art. Expression vectors may also contain a ribosome binding site for translation initiation, and a transcription terminator. The vector may also contain sequences useful for the amplification of gene expression.

Regulatory transcript termination regions may be provided in expression constructs of this invention as well. Transcript termination regions may be provided by the DNA sequence encoding the WS/DGAT or a convenient transcription termination region derived from a different gene source, for example, the transcript termination region which is naturally associated with the transcript initiation region. The skilled artisan will recognize that any convenient transcript termination region which is capable of terminating transcription in a host cell may be employed in the constructs of the present invention.

Expression and cloning vectors can and usually do contain a structural gene or selection marker having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species into which the expression construct or components thereof are introduced, one or more markers may be employed, where different conditions for selection are used for the different hosts.

Non-limiting examples of suitable selection markers include genes that confer resistance to bleomycin, gentamycin, glypho sate, hygromycin, kanamycin, methotrex ate, nalidixic acid, phleomycin, phosphinotricin, spectinomycin, streptomycin, sulfonamide, sulfonylureas, and tetracycline. Maliga et al. (1995). Examples of markers include, but are not limited to, alkaline phosphatase (AP), myc, hemagglutinin (HA), β glucuronidase (GUS), luciferase, and green fluorescent protein (GFP). In one embodiment, the vectors contain structural genes providing resistance to kanamycin and nalidixic acid.

In addition, expression vectors can also contain marker sequences operatively linked to a nucleotide sequence for a protein that encode an additional protein used as a marker. The result is a hybrid or fusion protein comprising two linked and different proteins. The marker protein can provide, for example, an immunological or enzymatic marker for the recombinant protein produced by the expression vector.

Additionally, the end of the polynucleotide can be modified by the addition of a sequence encoding an amino acid sequence useful for purification of the protein produced by affinity chromatography. Various methods have been devised for the addition of such affinity purification moieties to proteins. Representative examples can be found in U.S. Pat. Nos. 4,703,004, 4,782,137, 4,845,341, 5,935,824, and 5,594,115. Any method known in the art for the addition of nucleotide sequences encoding purification moieties can be used, for example those contained in Innis et al. (1990); Sambrook et al. (2001). More specifically, one embodiment of the present invention provides expression constructs containing the nucleotide sequence represented in SEQ ID NO:1. Such constructs are prepared as demonstrated in the Examples below.

More particularly, the present invention includes recombinant constructs comprising the isolated polynucleotide sequence of the present invention. The constructs can include a vector, such as a plasmid or viral vector, into which the sequence of the present invention has been inserted, either in the forward or reverse orientation. The recombinant construct further comprises regulatory sequences, including for example, a promoter operatively linked to the sequence. Large numbers of suitable vectors and promoters are known to those skilled in the art and are commercially available. In one preferred embodiment, the pCS2+, the pCEP4 (Invitrogen) and the pIRESneo (Clontech) vectors are used. It will be understood by those skilled in the art, however, that other plasmids or vectors may be used as long as they are replicable and viable or capable of expressing the encoded protein in the host.

The polynucleotide sequence of the present invention can also be part of an expression cassette that at a minimum comprises, operably linked in the 5' to 3' direction, a promoter, a polynucleotide of the present invention, and a transcriptional termination signal sequence functional in a host cell. The promoter can be of any of the types discussed herein, for example, a tissue specific promoter, a developmentally regulated promoter, an organelle specific promoter, etc. The expression cassette can further comprise an operably linked targeting sequence, transit or secretion peptide coding region capable of directing transport of the protein produced. The expression cassette can also further comprise a nucleotide sequence encoding a selectable marker and a purification moiety.

A further embodiment of the present invention relates to transformed host cells containing the constructs comprising the polynucleotide sequence of the present invention. The host cell can be a higher eukaryotic cell, such as a mammalian or a plant cell, or a lower eukaryotic cell such as an insect cell or a yeast cell, or the host can be a prokaryotic cell such, as a bacterial cell. In one embodiment, the host cell is a bacterial cell. In one embodiment, the host cell is an *E. coli* cell or a *P. citronellolis* cell. Introduction of the construct into the host cell can be accomplished by a variety of methods including calcium phosphate transfection, DEAE-dextran mediated transfection, Polybrene mediated transfection, protoplast fusion, liposome mediated transfection, direct microinjection into the nuclei, biolistic (gene gun) devices, scrape loading, and electroporation.

The present invention also relates to proteins encoded by the isolated polynucleotides. As used herein the term protein includes fragments, analogs and derivatives of the wax ester synthase-like protein. The terms "fragment," "derivative" and "analog" as used herein mean a polypeptide that retains essentially the same biological function or activity as the wax ester synthase/DGAT encoded by the sequence of the present invention. For example, an analog includes a pro-protein which can be cleaved to produce an active mature protein. The protein of the present invention can be a natural protein, a recombinant protein or a synthetic protein or a polypeptide.

Those of ordinary skill in the art are aware that modifications in the amino acid sequence of a peptide, polypeptide, or protein can result in equivalent, or possibly improved, second generation peptides, etc., that display equivalent or superior functional characteristics when compared-to the original amino acid sequence. The present invention accordingly encompasses such modified amino acid sequences. Alterations can include amino acid insertions, deletions, substitutions, truncations, fusions, shuffling of subunit sequences, and the like, provided that the peptide sequences produced by such modifications have substantially the same functional properties as the naturally occurring counterpart sequences disclosed herein. Biological activity or function can be determined by, for example, the ability of the protein to increase wax ester production in a host cell as depicted in the examples below.

One factor that can be considered in making such changes is the hydropathic index of amino acids. The importance of the hydropathic amino acid index in conferring interactive biological function on a protein has been discussed by Kyte and Doolittle (1982). It is accepted that the relative hydropathic character of amino acids contributes to the secondary structure of the resultant protein. This, in turn, affects the interaction of the protein with molecules such as enzymes, substrates, receptors, DNA, -antibodies, antigens, etc.

Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamane/aspartate/asparagine (−3.5); lysine (−3.9); and arginine (−4.5).

As is known in the art, certain amino acids in a peptide or protein can be substituted for other amino acids having a similar hydropathic index or score and produce a resultant peptide or protein having similar biological activity, i.e., which still retains biological functionality. In making such changes, it is preferable that amino acids having hydropathic indices within 2 are substituted for one another. More preferred substitutions are those wherein the amino acids have hydropathic indices within 1. Most preferred substitutions are those wherein the amino acids have hydropathic indices within 0.5.

Like amino acids can also be substituted on the basis of hydrophilicity. U.S. Pat. No. 4,554,101 discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0 1); serine (+0.3); asparagine/glutamane (+0.2); glycine (0); threonine (−0.4); proline (−0.5 1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4). Thus, one amino acid in a peptide, polypeptide, or protein can be substituted by another amino acid having a similar hydrophilicity score and still produce a resultant protein having similar biological activity, i.e., still retaining correct biological function. In making such changes, amino acids having hydropathic indices within 2 are preferably substituted for one another, those within 1 are more preferred, and those within 0.5 are most preferred.

As outlined above, amino acid substitutions in the peptides of the present invention can be based on the relative similarity of the amino acid side-chain substituents, for example, their hydrophobicity, hydrophilicity, charge, size, etc. Exemplary substitutions that take various of the foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and: (4) neutral non-polar amino acids such as alanine, leucine, isoleucine, valine, proline, phenylalanine, tryptophan, and methionine. It should be noted that changes which are not expected to be advantageous can also be useful if these result in the production of functional sequences.

The fragment, derivative or analog of the proteins encoded by the polynucleotide sequence of the present invention may be, for example and without limitation, (i) one in which one or more amino acid residues are substituted with a conserved or non-conserved amino acid residue, and such substituted amino acid residue may or may not be one encoded by the genetic code; (ii) one in which one or more of the amino acid residues includes a substituent group; (iii) one in which the mature protein is fused to another compound such as a compound to increase the half-life of the protein; (iv) one in which additional amino acids are fused to the protein to aid in purification or in detection and identification; or (v) one in which additional amino acid residues are fused to the protein to aid in modifying tissue distribution or localization of the protein to certain locations such as the cell membrane or extracellular compartments.

The term protein also includes forms of the protein to which one or more substituent groups have been added. A substituent is an atom or group of atoms that is introduced into a molecule by replacement of another atom or group of atoms. Such groups include, but are not limited to, lipids, phosphate groups, sugars and carbohydrates. Thus, the term protein includes, for example, lipoproteins, glycoproteins, phosphoproteins and phospholipoproteins.

The present invention also includes methods for the production of the protein of interest from cells transformed with a polynucleotide sequence of the present invention. Proteins can be expressed in mammalian cells, plant cells, insect cells, yeast, bacteria, bacteriophage, or other appropriate host cells. Host cells are genetically transformed to produce the protein of interest by introduction of an expression vector containing the nucleic acid sequence of interest. The characteristics of suitable cloning vectors and the methods for their introduction into host cells have been previously discussed. Alternatively, cell-free translation systems can also be employed using RNA derived from the DNA of interest. Methods for cell free translation are known to those skilled in the art. (Davis et al., 1986; Ausubel et al., 1992).

Host cells are grown under appropriate conditions to a suitable cell density. If the sequence of interest is operably linked to an inducible promoter, the appropriate environmental alteration is made to induce expression. If the protein accumulates in the host cell, the cells are harvested by, for example, centrifugation or filtration. The cells are then disrupted by physical or chemical means to release the protein into the cell extract from which the protein can be purified. If the host cells secrete the protein into the medium, the cells and medium are separated and the medium retained for purification of the protein.

Larger quantities of protein can be obtained from cells carrying amplified copies of the sequence of interest. In this method, the sequence is contained in a vector that carries a selectable marker and transfected into the host cell or the selectable marker is co-transfected into the host cell along with the sequence of interest. Lines of host cells are then selected in which the number of copies of the sequence have been amplified. A number of suitable selectable markers will be readily apparent to those skilled in the art. For example, the dihydrofolate reductase (DHFR) marker is widely used for co-amplification. Exerting selection pressure on host cells by increasing concentrations of methotrexate can result in cells that carry up to 1000 copies of the DHFR gene.

Proteins recovered can be purified by a variety of commonly used methods, including, but not limited to, ammonium sulfate precipitation, immuno precipitation, ethanol or acetone precipitation, acid extraction, ion exchange chromatography, size exclusion chromatography, affinity chromatography, high performance liquid chromatography, electrophoresis, thin layer chromatography, and ultra filtration. If required, protein refolding systems can be used to complete the configuration of the protein.

The wax ester synthase/DGAT protein encoded by the polynucleotide of SEQ ID NO:1 has been shown to catalyze the transfer of an acyl chain from fatty acyl-CoA to fatty alcohol via condensation of the fatty alcohol with the acyl-CoA and gave DGAT activity, thereby resulting in the formation of a wax ester (see Examples below) in several bacterial strains into which this sequence has been recombinantly introduced. Therefore, in one embodiment, a polynucleotide provided by the invention is employed to produce wax ester in bacteria at a relatively affordable cost. This wax ester, in turn, may be utilized in connection with a number of products including cosmetics, industrial lubricants, coatings, food products, livestock feed, and fermentation media. Livestock includes, but is not limited to, for example, sheep, mules, hogs, cattle, horses, and other grazing animals, or animals commonly raised for agricultural or food production purposes. Fermentation media includes, but is not limited to, for example, a growth media containing, a saccharide, such as glucose, a nitrogen source, a phosphorous source, and agar or other non-digestible polysaccharide, in which the processes of fermentation can occur.

As used in reference to a wax ester synthase protein of the present invention, the term "biological function" or "biological activity" refers to the ability of a wax ester synthase protein to catalyze the transfer of an acyl chain from fatty acyl-CoA to fatty alcohol via condensation of the fatty alcohol with the acyl-CoA, as well as the bifunctional DGAT activity, thereby resulting in the formation of a wax ester.

As used herein, the terms "complementary" or "complementarity" refer to the pairing of bases, purines and pyrimidines, that associate through hydrogen bonding in double stranded nucleic acid. The following base pairs are complementary: guanine and cytosine; adenine and thymine; and adenine and uracil. As used herein the terms include complete and partial complementarity.

As used herein, the term "hybridization" refers to a process in which a strand of nucleic acid joins with a complementary strand through base pairing. The conditions employed in the hybridization of two non-identical, but very similar, complementary nucleic acids vary with the degree of complementarity of the two strands and the length of the strands. Thus the term contemplates partial as well as complete hybridization. Such techniques and conditions are well known to practitioners in this field and further described herein.

As used herein, the term "amino acid" is used in its broadest sense, and includes naturally occurring amino acids as well as non-naturally occurring amino acids, including amino acid analogs and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid analogs and derivatives; naturally occurring non-proteogenic amino acids such as norleucine, -alanine, ornithine, etc.; and chemically synthesized compounds having properties known in the art to be characteristic of amino acids.

As used herein, the term "proteogenic" indicates that the amino acid can be incorporated into a peptide, polypeptide, or protein in a cell through a metabolic pathway.

As used herein, "expression cassette" means a genetic module comprising a gene and the regulatory regions necessary for its expression, which may be incorporated into a vector.

As used herein, "secretion sequence" or "signal peptide" or "signal sequence" means a sequence that directs newly synthesized secretory or membrane proteins to and through membranes of the endoplasmic reticulum, or from the cytoplasm to the periplasm across the inner membrane of bacteria, or from the matrix of mitochondria into the inner space, or from the stroma of chloroplasts into the thylakoid. Fusion of such a sequence to a gene that is to be expressed in a heterologous host ensures secretion of the recombinant protein from the host cell.

As used herein, a "recombinant nucleic acid" is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequences derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design.

As used herein, "polynucleotide" and "oligonucleotide" are used interchangeably and mean a polymer of at least 2 nucleotides joined together by phosphodiester bonds and may consist of either ribonucleotides or deoxyribonucleotides.

As used herein, "sequence" means the linear order in which monomers occur in a polymer, for example, the order of amino acids in a polypeptide or the order of nucleotides in a polynucleotide.

As used herein, "peptide" and "protein" are used interchangeably and mean a compound that consists of two or more amino acids that are linked by means of peptide bonds.

As used herein "recombinant protein" means that the protein, whether comprising a native or mutant primary amino acid sequence, is obtained by expression of a gene carried by a recombinant DNA molecule in a cell other than the cell in which that gene and/or protein is naturally found. In other words, the gene is heterologous to the host in which it is expressed. It should be noted that any alteration of a gene, including the addition of a polynucleotide encoding an affinity purification moiety to the gene, makes that gene unnatural for the purposes of this definition, and thus that gene cannot be "naturally" found in any cell.

As used herein, "targeting sequence" means in the context of gene or polynucleotide insertion, a sequence which results in the gene or polynucleotide being inserted at a particular location by homologous recombination. In the context of proteins or peptides, "targeting sequence" refers to a nucleotide sequence encoding an amino acid sequence the presence of which results in a protein being directed to a particular destination within a cell.

As used herein, "upstream region" means a segment of a polynucleotide that is 5' to a point of reference on the same polynucleotide.

As used herein, "downstream region" means a segment of a polynucleotide that is 3' to a point of reference on the same polynucleotide.

As used herein, the terms "construct" and "vector" are used interchangeably.

The detailed description set-forth above is provided to aid those skilled in the art in practicing the present invention. Even so, this detailed description should not be construed to-unduly limit the present invention as modifications and variation in the embodiments discussed herein-can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

Example 1

Materials and Methods

A. Bacterial Strains, Plasmids, Media and Growth Conditions

The bacterial strains and plasmids used in this study are listed in Table 1. Cells of *A. calcoaceticus* were cultivated aerobically in Luria-Bertani (LB) medium. (Sambrook et al., 2001) in Erlenmeyer flasks without baffles at 30° C. For the induction of wax ester formation cells were cultivated in mineral salts medium (MSM) (Schlegel et al., 1961) with 0.1 g $l^{-1}$ $NH_4Cl$ and 1% (w/v) sodium gluconate as carbon source. These culture conditions are referred to as "storage conditions". Cells of *E. coli* were grown at 37° C. in LB medium. *P. citronellolis* was cultivated in LB medium at 30° C. Solidified media contained 1.8% (w/v) agar. Antibiotics were added at the following concentrations if appropriate: ampicillin (Ap) 75 µg $ml^{-1}$, nalidixic acid (Ndx) 10 µg $ml^{-1}$, kanamycin (Km) 50 µg $ml^{-1}$, tetracycline (Tc) 12.5 µg $ml^{-1}$.

TABLE 1

Bacterial strains and plasmids used in this study

| Bacterial strain or plasmid | Relevant characteristics | Source or reference |
| --- | --- | --- |
| Bacteria: *Acinetobacter calcoaceticus* | | |
| BD413 | unencapsulated mutant of BD4; wax+ | ATCC 33305; Juni and Janik, 1969 |
| BD413 ($Ndx^r$) | spontaneous $Ndx^r$ mutant of BD413 | This study |
| ACM7 | miniTn10Km-induced wax$^-$ mutant of BD413 ($Ndx^r$) | This study |
| BD413waxΩKm | wax knock-out mutant of BD413 | This study |
| *Escherichia coli* | | |
| XL1-Blue | recA1, endA1, gyrA96, thi-1, hsdR17, ($r^-k$ $m^- 7_k$), supE44, relA1, λ$^-$, lac$^-$ [F'proABlacI$^q$ZΔMS, $Tn^{10}$(tet)] | Bullock, 1987 |

TABLE 1-continued

Bacterial strains and plasmids used in this study

| Bacterial strain or plasmid | Relevant characteristics | Source or reference |
|---|---|---|
| S17-1 | recA; harbours the tra genes of plasmid RP4 in the chromosome; proA, thi-1 | Simon et al., 1983, |
| SM10(λpir) | thi-1, thr, leu, tonA, lacY, supE, recA::RP4-2-Tc::Mu, Km$^r$, λpir | Miller and Mekalanos, 1988, |
| *Pseudomona citronellolis* | Wild-type, wax$^-$ | DSM 50332 |
| Plasmids: | | |
| PLOFKm | MiniTn10Km delivery plasmid, Ap$^r$, Km$^r$ oriR6K, mobRP4 | Herrero et al., 1990, |
| PHC79 | Cosmid, Ap$^r$, Tc$^r$ | Hohn and Collins, 1980 |
| PHC79: E8 | MiniTn10Km-harbouring EcoR1 fragment 24 from ACM7 | This study |
| Pbluescript SK$^-$ | Ap$^r$, lacPOZ; T7 and T3 promoter | Stratagene |
| Pbluescript KS$^-$ | Apr, lacPOZ; T7 and T3 promoter | Stratagene |
| PSK: waxEB19 | PCR™-amplified 1.9-kbp BamHI-EcoRI fragment comprising wax in pBluescript SK$^-$ | This study |
| PKS: waxEB19 | PCR™-amplified 1.9-kbp BamHI-EcoRI fragment comprising wax in pBluescript KS$^-$ | This study |
| PSKsymΩKm | ΩKm in pSKsym wax disrupted by insertion of ΩKm in pBluescript SK$^-$ | Overhage et al., 1999 This study |
| PKS: wax | PCR™-amplified 1.5-kbp wax with sequence in pBluescript KS$^-$ | This study |
| PKS: wax-His$_6$C | PCR™-amplified 1.5-kbp wax with S/D sequence and C-terminal His6-tag in pBluescript KS$^-$ | This study |
| PSER200-4 | *A. calcoacefcus* expression vector; Km$^r$ | Reiser and Somerville, 1997 |
| PSER200-4; wax | PCR™-amplified 1.9-kbp BamHI-EcoRI fragment comprising wax in pSER200-4 | This study |
| PBBRIMCS-2 | broad host range, Km$^r$, IacPOZ | Kovach et al., 1995 |
| PBBRIMCS-2: wax | PCR™-amplified 1.5-kbp wax with S/D Sequence in pBBRIMCS-2 | This study |

B. miniTn10Km Mutagenesis miniTn10Km-induced mutants of *A. calcoaceticus* BD413 (Ndxr) were created according to Herrero et al. (1990) employing the transposon delivery suicide plasmid pLOFKm which was transferred from *E. coli* SM10 (λpir) to *A. calcoaceticus* BD413 (Ndx$^r$) by conjugation by the spot mating technique. Mixtures of donor and recipient were spotted at a 1:1 ratio on LB agar plates containing 50 μM isopopyl-β-D-thiogalactopyranoside (IPTG) for induction of the ISIO$_R$ transposase, which is controlled by the ptac promoter, and were incubated for 16 h at 30° C. Cells were suspended in 10 mM MgSO$_4$, and appropriate dilutions were plated on MSM plates containing 1% (w/v) sodium gluconate, 50 μg Km ml$^{-1}$ and 10 μg Ndx ml$^{-1}$ for selection of transposon-insertion mutants of *A. calcoaceticus* BD413 (Ndx$^r$) excluding the presence of auxotrophic mutants.

C. Mutant Screening with Sudan Black B Staining

Mutants of *A. calcoaceticus* BD413 (Ndx$^r$) defective in the accumulation of wax esters were identified in accordance to Reiser and Somerville (1997). Mutagenized cells were replica plated onto MSM plates containing 1% (w/v) sodium-gluconate and on LB master plates and were incubated for 48 h at 30° C. to induce wax ester accumulation. The cells on the MSM agar plates were then stained by irrigating the plates-with a 0.02% (w/v) Sudan Black B solution in 50:4:5 (v/v/v) dimethyl sulfoxide-ethanol-water and gently shaking them for 30 min. After this step, the staining solution was disposed, and the plates were carefully washed by gently shaking them for 5 min with 70% (v/v) ethanol. Lighter-staining colonies were identified on these plates, and the corresponding colonies from the master plates were subsequently analyzed by thin-layer chromatography (TLC).

D. Thin-Layer Chromatography (TLC)

Cultures of 50 ml MSM with 1% (w/v) sodium gluconate were inoculated with 3 ml of an overnight LB preculture of *A. calcoaceticus* and incubated for 24 h at 30° C. Cells were harvested by centrifugation and lyophilized. Neutral lipids were isolated from the cells by extracting 1.5 mg lyophilized cell material with 100 µl chloroform/methanol (1:1, v/v) followed by centrifugation at 13,000 rpm for 2 min. 50 µl of the organic phase were spotted onto a silica gel 60 TLC plate (Merck, Darmstadt, Germany) and the neutral lipids were separated by developing the plates in hexane:diethylether: acetic acid (90:15:1, v/v/v). Lipid spots were visualized by spraying the plates with 40% (v/v) sulfuric acid and charring over a Bunsen flame or by exposition to iodine vapor.

E. Isolation and Manipulation of DNA

Chromosomal DNA of miniTn10Km-induced mutants of *A. calcoaceticus* BD413 (Ndx$^r$) was isolated by the method of Marmur (1961). Plasmid DNA was isolated by the method of Bimboim and Doly (1979). DNA restriction fragments were purified from agarose gels using the Nucleotrap-Kit (Macherey-Nagel,Düren, Germany) following the instructions provided by the manufacturer. Restriction enzymes, T4-ligase and other DNA-manipulating enzymes were purchased from GibcoBRL (Karlsruhe, Germany) and used according to the manufacturer's instructions.

F. Transfer of DNA

Competent cells of *E. coli* were prepared and transformed by the CaCl$_2$ procedure as described by Hanahan (1983). Transduction of genomic DNA of *A. calcoaceticus* BD413, which was ligated into cosmid pHC79 DNA, to *E. coli* S 17-1 was done as described by Hohn and Murray (1977) after in vitro packaging into λ phages employing the Gigapack III Gold packaging extract (Stratagene, Heidelberg, Germany). Conjugation of *E. coli* S 17-1 (donor) harbouring hybrid plasmids and *P. citronellolis* (recipient) was performed on solidified NB medium as described by Friedrich et al. (1981). *A. calcoaceticus* was transformed as described by Palmen et al. (1993) utilizing the high natural competence of this strain.

G. Genotypic Characterization of the miniTn10 km-Insertion Mutants of *A. calcoaceticus* BD413 (Ndx$^r$)

Genomic DNA of miniTn10Km-insertion mutants was digested with EcoRI, and the genomic EcoRI fragments were ligated to cosmid pHC79 DNA. After in vitro packaging in; λ phages the recombinant cosmids were transduced into *E. coli* S17-1. Recombinant *E. coli* clones were selected by their Km resistance conferred by the miniTn10Km insertion. The hybrid cosmids were isolated, digested with EcoRI and ligated into the plasmid pBluescript SK. The recombinant plasmids were transformed into *E. coli* XL1-Blue, and clones resistant to Km plus Ap were selected. The resulting hybrid plasmids were isolated and digested with EcoRI and NotI, which cuts up- and downstream of the Km resistance gene being part of miniTn10Km (Herrero et al. 1990). The resulting fragments were subcloned into EcoRI and NotI digested pBluescript SK and transformed into *E. coli* XL1-Blue. The obtained hybrid plasmids contained a EcoRI-NotI fragment which included IS10$_R$ or IS10$_L$, respectively, plus genomic DNA adjacent to the miniTn10Km insertion. The miniTn10Km insertion locus was determined by DNA sequence analysis of the recombinant plasmids using sequencing primers specific to pBluescript SK.

H. DNA Sequencing and Sequence Data Analysis

The dideoxy chain-termination method (Sanger et al., 1977) was used to determine the DNA sequence employing the Sequi Therm EXCEL TM II long-read cycle sequencing kit (Biozym, Hessisch Oldendorf, Germany) and - - - :

IRD800-labelled oligonucleotides (MWG-Biotech, Ebersberg, Germany). The primer hopping strategy (Strauss et al., 1986) was applied. Sequencing was performed with a LI-COR DNA model 4000L automatic sequencer (MWG-Biotech, Ebersberg, Germany). Sequence data were compared with sequences deposited in the GeneBank database (online available at www.ncbi.nlm.nih.gov) using the program BlastSearch 2.0.10. (Altschul et al., 1997). Preliminary sequence data from the *A. calcoaceticus* BD413 genome project were obtained online from www.genoscope.fr and analyzed with the online program pack Biology WorkBench 3.2 at workbench.sdsc.edu.

I. PCR™ Amplifications

PCR™ amplifications of plasmid or genomic encoded DNA were performed according to Sambrook et al. (2001) in a PCR™ Sprint thermocycler (Hybaid, Teddington, UK) with Platinum Pfx DNA polymerase (GibcoBRL, Karlsruhe, Germany).

J. Cloning of wax/dgat and Functional Heterologous Expression

The coding region of the wax/dgat gene including the up- and downstream regions was amplified by tailored PCR™ from genomic DNA of *A. calcoaceticus* BD413 applying the following oligonucleotides: 5'-AAA<u>GAATTC</u>TGGCCTACATGCAGGCAACTTAA-3' (5' end) (SEQ ID NO:5) and 5'-TTT<u>GGATCC</u>GAATTTTCAATACTAGGTACACA-3' (3' end) (SEQ ID NO:6) introducing EcoRI and BamHI restriction sites (underlined), respectively. The obtained 1908-bp PCR™ product, shown in FIG. 5 (SEQ ID NO:3), was cloned into EcoRI and BamHI restricted pBluescript KS collinear to the lacZ promoter, resulting in pKS:waxEB 19. Additionally, the obtained 1908-bp PCR™ product was cloned into EcoRI and BamHI restricted pSER200-4, resulting in pSER200-4:wax.

The coding region of the wax/dgat gene without upstream region was amplified by tailored PCR™ from genomic DNA of *A. calcoaceticus* BD413 applying the following oligonucleotides: 5'-AAA<u>GAATTC</u><u><u>AAGGAGG</u></u>TATCCACGCTATGCGCCCATTAC-3' (5' end) (SEQ ID NO:7) introducing a EcoRI restriction site (underlined) and a ribosome binding site (double underlined) and 5'-TT<u>GGATCC</u>AGGGCTAATTTAGCCCTTTAGTT-3' (3' end) (SEQ ID NO:8) introducing a BamHI restriction site (underlined). The obtained 1470-bp PCR™ product, shown in FIG. 6 (SEQ ID NO:2), was cloned into EcoRI and BamHI restricted pBluescript KS collinear to the lacZ promoter, resulting in pKS:wax. Additionally, the 1470-bp PCR™ product was cloned into EcoRI and BamHI restricted pBBRIMCS-2 collinear to the lacZ promoter, resulting in pBBRIMCS-2:wax.

For amplification of a DNA fragment encoding a C-terminal His$_6$-tagged wax ester-synthase by tailored PCR™ using pKS:wax as template, the following oligonucleotides were applied: 5'-AAA<u>GAATTC</u><u><u>AAGGAGG</u></u>TATCCACGCTATGCGCCCATTAC-3' (5' end) (SEQ ID NO:9) introducing a EcoRI restriction site (underlined) and a ribosome binding site (double underlined) and '-TTT<u>GGATCC</u>TTAGTGGTGGTGGTGGTGGTGATTGGCTGTTTT AATATCTTCCT-3' (3' end) (SEQ ID NO:10) introducing a BamHI restriction site (underlined) and the His6-tag. The obtained 1430-bp PCR™, product was cloned into EcoRI and BamHI restricted pBluescript KS" collinear to the lacZ promoter, resulting in pKS:wax-His$_6$C.

Cells of *E. coli* harbouring pBluescript KS, pBBR1MCS-2, pKS:waxEB19, pKS:wax, pBBR1MCS-2:wax and pKS:wax-His$_6$C were cultivated in 50 ml LB medium inoculated with 1% (v/v) of an overnight LB preculture for 6 h at 37° C. in the presence of 1 mM IPTG and appropriate antibiotics. *P. citronellolis* harbouring pBBR1MCS-2 and pBBR1MCS-2:wax was cultivated in 50 ml LB medium inoculated with 1% (v/v) of an overnight LB preculture for 6 h at 37° C. in the presence of 50 μg Km ml$^{-1}$. Cells were harvested by centrifugation (10 min, 4,500 rpm at 4° C.), washed with 125 mM sodium phosphate buffer (pH 7.4) and resuspended in 1 ml of the same buffer. Crude extracts were obtained as described below.

50 ml MSM according to Schlegel et al. (1961) were inoculated with 2 ml of LB precultures of *P. citronellolis* DSM 50332 harbouring pBBRIMCS-2 and pBBRIMCS-2:wax, respectively, and incubated for 48 h at 30° C. with 0.3% (w/v) hexadecanol and 0.3% (w/v) hexadecanol plus 0.5% (w/v) gluconate as carbon sources. Cells were harvested by centrifugation, lyophilized and analyzed for the production of wax esters by TLC.

K. Inactivation of the Wax/dgat Gene of *A. calcoaceticus* BD413 by Insertion of ΩKm For inactivation of the wax/dgat gene by insertion of ΩKm, the 1908-bp PCR™ product described above was cloned into EcoRI and BamHI restricted pBluescript SIC, resulting in—pSK:waxEB19. This hybrid plasmid was restricted with NruI, which cuts within the wax/dgat gene, and ligated with ΩKm, which was recovered by SmaI digestion of plasmid pSKsymΩKm (Overhage et al., 1999), resulting in the hybrid plasmid pSK:waxΩKm. The disrupted wax/dgat gene was isolated from pSK:waxΩKm by digestion with EcoRI and BaMHI and the linear DNA fragment was transformed to *A. calcoaceticus* BD413. Transformants were selected on LB plates containing 50 μg Km ml$^{-1}$. The correct exchange of the wax/dgat gene with the disrupted gene in the obtained knock-out strain *A. calcoaceticus*. BD413waxΩKm was proven by PCR™ using the oligonucleotide primers 5'-AAAGAATTCAAG-GAGGTATCCACGCTATGCGCCCATTAC-3' (5' end) (SEQ ID NO:11) and 5'-TTTGGATCCAGGGCTAATT-TAGCCCTTTAGTT-3' (3' end) (SEQ ID NO:12) resulting in a single PCR™ product with the expected size of 2.5 kbp.

L. Preparation of Crude Extracts and Subcellular Fractions

Cells were disrupted by ultrasonification in a Sonopuls GM 200 (Bandelin, Berlin, Germany) with an amplitude of 16 μm (1 min ml$^{-1}$). Samples were cooled on ice during ultrasonification. Insoluble and soluble protein fractions were obtained after ultracentrifugation at 35,000 g for 30 min. Protein concentrations were determined by the method of Madford (1976). Bovine serum albumin (BSA) fraction V was used as standard.

M. Termination of Wax Ester Synthase Activity

Cells of *E. coli* were grown for determination of the wax ester synthase activity in the presence of IPTG or in the case of *P. citronellolis* without IPTG as described above. Measurement of the wax ester synthase activity in *A. calcoaceticus* was done with cells grown under storage conditions at 30° C. for 24 h. Crude extracts were obtained as described above. Activity of the wax ester synthase was measured in a total volume of 250 μl containing 3.75 mM 1-hexadecanol, 4.63 mg ml$^{-1}$ BSA, 10 mM MgCl$_2$, 4.72 μM 1-$^{14}$C-Palmitoyl-CoA (specific activity 1.961 Bq pmol$^{-1}$) and 125 mM sodium phosphate buffer (pH 7.4). Hexadecanol and BSA were emulsified by ultrasonification. The assays were incubated at 35° C. for 30 min, and the reactions were stopped by extraction with 500 μl chloroform/methanol (1:1, v/v) for 1 min. After centrifugation the chloroform phase was withdrawn, evaporated to dryness, and 40 μg of chloroform-dissolved unlabeled reference wax ester (cetylpalmitate) were added. The lipids were separated by TLC applying hexane:diethylether:acetic acid (90:15:1, v/v/v) as solvent system. After staining the TLC plate with iodine vapor, the spots corresponding to waxes were scraped from the plates into scintillation vials, mixed with 5 ml of liquid scintillation counting cocktail lipoluma (J. T. Baker, Deventer, Netherlands), and radioactivity was measured using a model LS6500 scintillation counter (Beckmann Instruments, Munich, Germany).

Example 2

Results

A. Isolation of Wax-Negative (Wax) Mutants of *A. calcoaceticus* BD413 (Ndx$^r$)

Transposon mutagenesis of an isolated spontaneous Ndx-resistant strain of *A. calcoaceticus* BD413 was performed to obtain mutants affected in the accumulation of wax esters. A total of 4000 miniTn10Km-induced mutants were obtained and screened by Sudan Black B staining for mutants with a reduced or lacking accumulation of storage lipids. Eight mutants were isolated exhibiting a lighter staining with the lipophilic dye Sudan Black B. TLC analysis of these mutants revealed that all of them were unable to accumulate wax esters under storage conditions but were still able to accumulate triacylglycerols (TAGS) to some extent (FIG. 1). These wax mutants were designated ACM for *Acinetobacter calcoaceticus* mutants.

Figure 2:
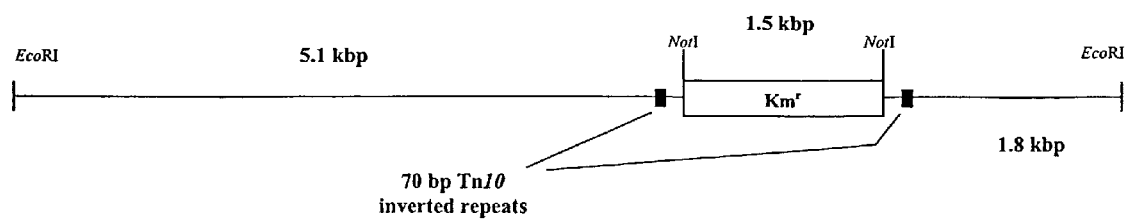
FIG. 2 shows the restriction pattern of the miniTn10Km-harboring 8.4-kbp EcoRI fragment isolated from wax$^-$mutants of *A. calcoaceticus* BD413 (Ndx$^r$).

B. Molecular Characterization of miniTn10Km-Induced Mutants Defective in Wax Esteraccumulation To map the insertions of miniTn10Km in these mutants, EcoRI fragments, which conferred resistance to Km, were cloned from genomic niutarit DNA. A 8.4-kbp EcoRI fragment was obtained for all eight mutants. For determination of the insertion sequences the 8.4-kbp EcoRI fragments were NotI digested resulting in a 5.1-kbp and a 1.8-kbp EcoRI-NotI fragment for all mutants (FIG. 2), which were subsequently subcloned into pBluescript SK. DNA sequence analyses of the transposon insertion loci revealed that miniTn10Km had inserted in the identical position in all analyzed mutants which makes it very likely that all mutants constitutes siblings. Therefore, only one mutant (ACM7) was selected for the subsequent detailed analyses. Transposon miniTn10Km had inserted with a 9 by palindromic direct repeat (5'-GCGTATGCG-3') (SEQ ID NO:13) immediately upstream of an ORF with the start codon ATG being part of the direct repeat. The putative translational product exhibited highest homology (37%) to the hypothetical 48.4-kDa protein Rv3740c from *Mycobacterium tuberculosis* H37Rv which belongs to a group of conserved hypothetical proteins in this strain (Cole et al. 1998a; Cole et al. 1998b). Further sequence comparison of the translational product to *Mycobacterium tuberculosis* H37Rv and *Arabidopsis thaliana* revealed several particularly well conserved stretches of amino acids (amino acids 132–139, 258–263, 267–273, 283–289, 373–379, 380388 in SEQ ID NO:4). These conserved amino acid sequences are HHAXVDGV (SEQ ID NO:16), NDVVLA (SEQ ID NO:17), GALRXYL (SEQ ID NO:18), PLXAMVP (SEQ ID NO:19), ISNVPGP (SEQ ID NO:20), and REPLYXNGA (SEQ ID NO:21), wherein "X" is any amino acid.

Figure 3:
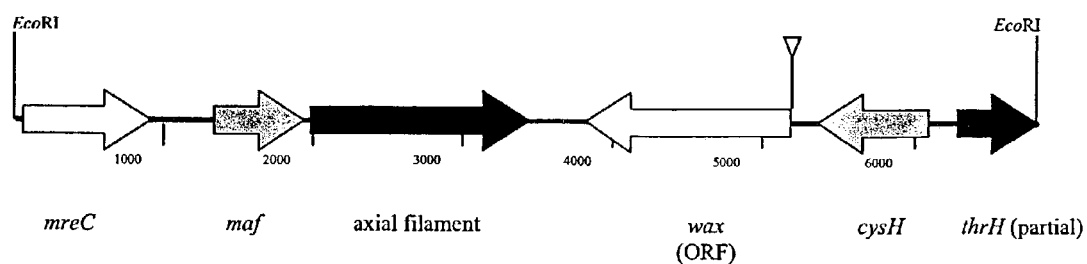
FIG. 3 shows the molecular organization of the 6.9-kbp EcoRI-fragment harboring the wax open reading frame from *A. calcoaceticus* BD413. The insertion locus of miniTn10Km is indicated by the triangle.

By sequence comparison of the miniTn10Km harbouring 8.4-kbp EcoRI fragment with the genome sequence data of *A. calcoaceticus* BD413, the DNA sequence of the native 6.9-kbp EcoRI fragment was obtained which revealed the molecular organization shown in FIG. 3. The hypothetical ORF was obviously not clustered with any genes whose putative translational products might be involved in the biosynthesis of wax esters (FIG. 3 and Table 2).

TABLE 2

Identified ORFs on the 6.9-kbp genomic EcoRI-fragment from *A. calcoaceticus* BD413 harboring the wax gene

| Gene designation | Highest homology to | Identical amino acids |
|---|---|---|
| MreC | Rod-shape determining protein MreC From *P. fluorescens* | 36% |
| Maf | Putative inhibitor of septum Formation Maf from *Salmonella Typhimurium* LT2 | 45% |
| axial filament | Cytoplasmic axial filament protein PA4477 from *P. aeruginosa* PAO1 | 58% |
| Wax | Hypothetical 48.4-kDa protein Rv3740c from *Mycobacterium Tuberculosis* H37Rv | 37% |
| CysH | 3'-phosphoadenosine-5'-phosphosul- Fate reductase (DAPS reductase) CysH from *P. aeruginosa* | 64% |
| thrH (partial) | Homoserine-Kinase ThrH (partial) From *P. aeruginosa* PAO1 | 68% |

Figure 4:
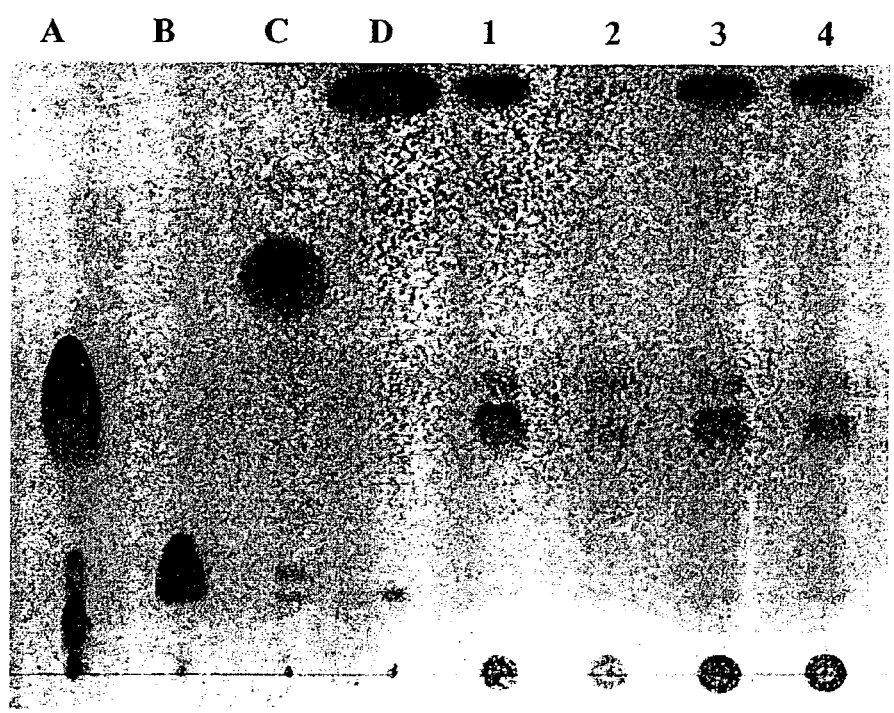
FIG. 4 shows the influence of the wax gene on storage lipid accumulation in *A. calcoaceticus* BD413. Cells were cultivated under storage conditions for 24 h. Lane A, TAG; Lane B, hexadecanol; Lane C, hexadecanal, Lane D, cetylpalmitate; Lane 1, *A. calcoaceticus* BD413; Lane 2, *A. calcoaceticus* BD413waxΩKm; Lane 3, *A. calcoaceticus* BD413 (pSER200-4); Lane 4, *A. calcoaceticus* BD413 (pSER200-4:wax).

C. Inactivation of the ORF (Wax) from *A. calcoaceticus* BD413 Adjacent to the miniTn10Km Insertion in Wax Mutants Since the miniTn10Km insertion mapped 5 by upstream of the ATG start codon of an hypothetical ORF in the wax" mutants but leaving the gene itself intact, the phenotype of a mutant with a defective ORF was unknown. Therefore, ORF was disrupted by insertion of the ΩKm gene and a knock-out strain of *A. calcoaceticus* BD413 was generated as described in Materials and Methods. The obtained strain *A. calcoaceticus* BD413waxΩKm was analyzed by TLC for its ability to accumulate wax esters under storage conditions. Inactivation of the hypothetical ORF led to the loss of wax ester accumulation whereas TAGs were still produced to some extent (FIG. 4). Thus, the knock-out strain exhibited the same phenotype than the miniTn10Km-induced mutants. Attempts to complement *A. calcoaceticus* BD413waxΩKm chemically by feeding with the precursor substrates hexadecanal and hexadecanol failed in reconstituting wax ester biosynthesis indicating that the inactivation of the hypothetical ORF probably did not affect the biosynthesis of precursors. A 1.9-kbp fragment comprising the ORF was PCR™ amplified and cloned as a BamHI-EcoRI fragment into pSER200-4which allows constitutive low-level expression in *A. calcoaceticus*. (Reiser, 1996) resulting in pSER200-4: wax. *A. calcoaceticus* BD413 harbouring pSER200-4:wax overexpressing the ORF exhibited a twofold higher wax ester synthase activity than the wild-type (Table 3) but the amount of accumulated wax esters was unaltered as estimated by TLC (FIG. 4). Wax ester synthase activity in the wax mutants *A. calcoaceticus* ACM7 and *A. calcoaceticus* BD413waxΩKm dropped to only 1% of the wild-type level (Table 3).

TABLE 3

Wax ester synthase activity in crude extracts of different strains of *A. calcoaceticus*, *E. coli* and *P. citronellolis*. Values are mean values of experiments done in triplicate.

| Strain | Wax ester synthase activity [pmol (mg protein)$^{-1}$ min$^{-1}$] |
|---|---|
| *A. calcoaceticus* | |
| BD413 | 101.7 |
| ACM7 | 1.0 |
| BD413waxΩKm | 1.4 |
| BD413 (pSER200-4) | 82.6 |
| BD413 (pSER200-4: wax) | 199.4 |
| *E. coli* | |
| XL1-Blue (pBluescript KS$^-$) | 0.3 |
| XL1-Blue (pKS: wax) | 117.6 |
| XL1-Blue (pKS: wax-His$_6$C) | 20.0 |
| S17-1 (pBBRIMCS-2) | 0.5 |
| S17-1 (pBBRIMCS-2: wax) | 128.8 |
| *P. citronellolis* | |
| pBBRIMCS-2 | 0.5 |
| pBBRIMCS-2: wax | 149.7 |

D. Cloning and Heterologous Expression of the Wax/dgat Gene

From the results presented above it was concluded that the hypothetical ORF could possibly code for the wax ester synthase, which was therefore designated as wax. Thus, the coding region of ORF plus its up and downstream regions was amplified by PCR™, and the obtained 1908 bp PCR™ product was cloned into EcoRI and BamHI restricted pBluescript KS collinear to the lacZ promoter, resulting in pKS: waxEB 19. However, no wax ester synthase activity could be detected in crude extract IPTG-induced cells of recombinant *E. coli* XL1-Blue harboring pKS:waxEB 19. Since this could be due to the fact that the putative ribosome binding site (5'-GAGG-3') (SEQ ID NO:14) 11 bp upstream of the ATG start codon of the ORF (FIG. 5) was not recognized in *E. coli*, a truncated fragment was amplified by tailored PCR™ introducing a ribosome binding site for *E. coli* (5'-AAGGAGGT-3') (SEQ ID NO:15) 9 bp upstream of the ATG start codon(FIG. 6, SEQ ID NO:2), which was cloned as a BamHI-EcoRI fragment into pBluescript KS and pBBRIMCS-2, resulting in the construction of pKS:wax and pBBRIMCS-2:wax. These hybrid plasmids were transformed into *E. coli* XL1-Blue and *E. coli* S17-1, respectively, and wax ester synthase activity was measured in crude extracts of IPTG-induced cultures. The wax gene was functionally heterologously expressed in *E. coli* XL1-Blue (pKS:wax) as well as in *E. coli* S17-1 (pBBRIMCS-2:wax) resulting in an active wax ester synthase with activities of 117.6 and 128.8 pmol (mg protein min)$^{-1}$, respectively, whereas in the control strains harboring only the vectors activities of only 0.3 and 0.5 pmol (mg protein min)$^{-1}$, respectively, were determined (Table 3). The enzyme activity was almost equally distributed between the insoluble and soluble fraction of the crude extracts (data not shown). These data clearly show that the wax/dgat gene encodes for an active wax ester synthase. The activity in recombinant *E. coli* strains harboring the wax gene was even higher than in the origin strain *A. calcoaceticus* BD413 25 (Table 3).

Additionally, pBBRIMCS-2:wax was transferred conjugatively to *P. citronellolis*, a Gram-negative alkane degrading bacterium unable to accumulate wax esters. Also in this host the wax gene was expressed constitutively resulting in a wax ester synthase activity of 149.7 pmol (mg protein min)−1, whereas the control harboring only the vector exhibited an activity of only 0.5 pmol (mg protein min)−1. (Table 3).

Figure 7:
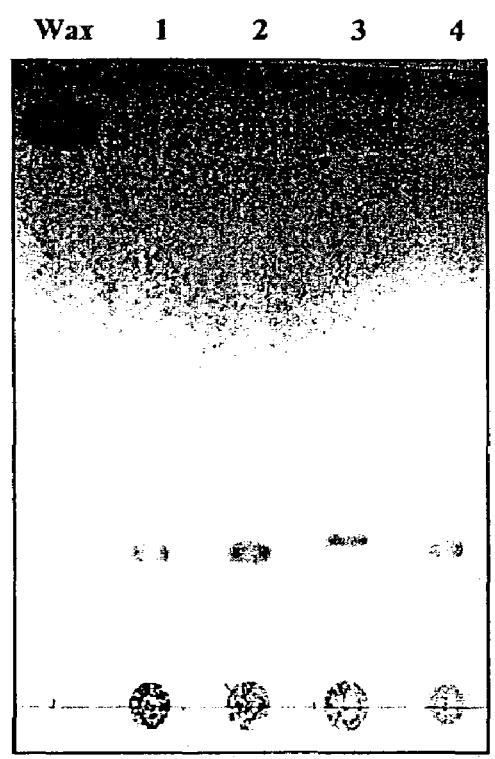
FIG. 7 is the recombinant wax ester biosynthesis in *P. citronellolis*. Cells were cultivated and analyzed by TLC as described in Materials and methods. Wax, cetylpalmitate standard; Lane 1: *P. citronellolis* (pBBRIMCS-2) cultivated with 0.3% (w/v) hexadecanol; Lane 2: *P. citronellolis* (pBBRIMCS-2) cultivated with 0.3% (w/v) hexadecanol plus 0.5% (w/v) gluconate; Lane 3: *P. citronellolis* (pBBRIMCS-2:wax) cultivated with 0.3% (w/v) hexadecanol; Lane 4: *P. citronellolis* (pBBRIMCS-2:wax) cultivated with 0.3% (w/v) hexadecanol plus 0.5% (w/v) gluconate.
Figure 11:
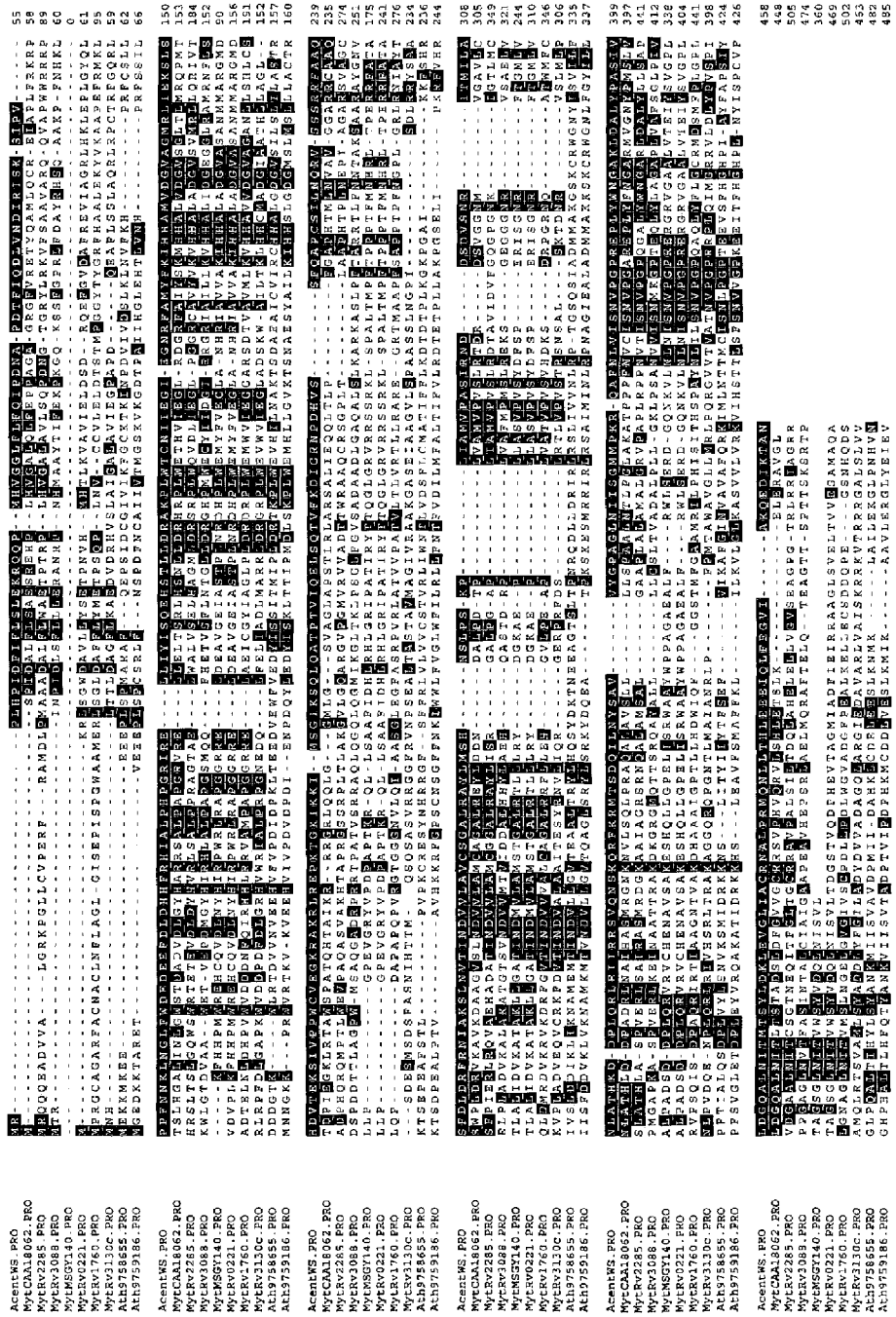
FIG. 11 shows an alignment of the polypeptide sequence encoded by SEQ ID NO:1 versus deduced *Arabidopsis thaliana* and bacterial sequences (SEQ ID NOs:22–31). Conserved regions are shown by shading.

Numerous Pseudomonas strains have been reported to be able to utilize n-alkanes as sole carbon source (Baptist et al., 1963; Macham and Heydeman, 1974; Williams et al., 1981). Alkane degradation route proceeds via successive terminal oxidations leading to the formation of the corresponding fatty alcohols, fatty aldehydes and fatty acids, which are subsequently esterified to the respective fatty acyl-CoA thioesters and channeled into the β-oxidation cycle (Baptist et al., 1963). The inventors tested a strain of *P. citronellolis*, for which the inventors have demonstrated heterologous expression of the *A. calcoaceticus* BD413 wax/dgat gene in a functionally active form (see Table 3), for its ability to utilize long-chain n-alkanes. This strain was able to grow on n-alkaes with chain-length from C 10 up to C 16 as sole carbon source (n-alkaes with chain-lengths longer than C 16 were not -tested) (data not shown). In addition, this strain could utilize also hexadecanol as an intermediate of the alkane degradation pathway as sole carbon source (data not shown). In *P. citronellolis* harbouring pBBRIMCS-2:wax, the cultivation in MSM with 0.3% (w/v) hexadecanol as sole carbon source led to the formation of small but significant amounts of wax esters as revealed by TLC analysis, whereas no wax esters were detectable in the control strain harbouring only the vector (FIG. 7). The uptake of hexadecanol into the cells, its oxidation to fatty acids via the alkane degradation pathway and their subsequent metabolization to acyl-CoA provided obviously sufficiently high intracellular levels of substrates of the wax ester synthase allowing the production of wax esters in the strain expressing the wax ester synthase from *A. calcoaceticus* BD413. However, no wax esters were formed when the cells were co-cultivated with 0.3% (w/v) hexadecanol plus 0.5% (w/v) gluconate (FIG. 7). Alkane oxidation activity has been reported to be subjected to carbon catabolite repression for various strains of *P. aeruginosa* (Dalhoff and Rehm, 1976; van der Linden, 1963; van Eyk and Bartels, 1968; *P. putida* (Fish et al., 1982; Grund et al., 1975; *P. oleovorans* (Staijen et al., 1999). The presence of gluconate has probably repressed the alkane degradation system in *P. citronellolis*. Therefore, no acyl-CoA thioesters could be formed from hexadecanol via the alkane degradation pathway during co-cultivation on 0.3% (w/v) hexadecanol plus 0.5% (w/v) gluconate, and thus the intracellular acyl-CoA level was to low to promote significant wax ester production in the strain expressing the wax ester synthase of *A. calcoaceticus* BD413 under this conditions.

E. Generation of $His_b$-Tagged Wax Ester Synthase and Purification of the Enzyme For the purpose of the purification of the wax ester synthase enzyme, pKS:wax-$His_6$C was constructed as described in Materials and Methods resulting in the expression of a C-terminal $His_6$-tagged protein. However, recombinant *E. coli* XL1-Blue (pKS:wax-$His_6$C) expressing the C-terminal $His_6$-tagged wax ester synthase exhibited only 17% activity in comparison to *E. coli* XL1-Blue harbouring the native wax/dgat gene on pKS:wax (Table 3). An attempt to purify the C-terminal $His_6$ tagged wax ester synthase chromatographafically using the Ni-NTA Spin Kit (Qiagen, Hilden, Germany) revealed only a very weak binding of the native enzyme on-the Ni-NTA column, resulting in an only 4.3-fold enrichment (data not shown). This indicates that the C-terminus of the protein is obviously not localized on the surface of the native enzyme but in the interior, which could explain that the addition of the 6 histidine residues to the C-terninus of the protein has such a strong negative effect on the enzyme activity.

Example 3

The Wax Gene Encodes a Bifunctional WS/DGAT

Wild-type *A. calcoaceticus* ADP1 exhibited a WS activity of 90.37 pmol (mg min)−1 and a ca. tenfold lower DGAT activity (Table 4), which corresponded approximately with the amounts of wax esters and TAGs accumulated under storage conditions as estimated by TLC. Inactivation of wax/dgat not only caused the loss of the ability for wax ester and TAG biosynthesis; it also abolished WS and DGAT activity in the transposon-induced mutant as well as in the knock-out mutant (Table 4).

TABLE 4

Shows WS and DGAT activities in crude cell extracts of different strains. Values are averages of at least three independent studies.

| Strain | | Plasmid | WS activity [pmol (mg min)$^{-1}$] | DGAT activity [pmol (mg min)$^{-1}$] |
|---|---|---|---|---|
| *A. calcoaceticus* | ADP1 | | 90.37 | 7.96 |
| | ACM7 | | 0.20 | 0.11 |
| | ADP1wax/dgat ΩKm | | 0.65 | 0.17 |
| *E. coli* | XL1-Blue | pBluescript KS− | 0.11 | 0.11 |
| | | pKS: wax/dgat | 84.51 | 9.37 |
| | | pBluescript SK− | 0.10 | 0.10 |
| | | pSK: wdh3269 | 0.65 | 0.31 |
| | S17-1 | pBBRIMCS-2 | 0.11 | 0.10 |
| | | pBBRIMCS-2: wax/dgat | 99.20 | 25.03 |
| *P. citronellolis* | | pBBRIMCS-2 | 0.10 | 0.10 |
| | | pBBRIMCS-2: wax/dgat | 99.20 | 25.03 |
| *P. citronellolis* | | pBBRIMCS-2 | 0.10 | 0.10 |
| *M. smegmatis* | mc$^2$155 | | 106.54 | 96.44 |
| *R. opacus* | PD630 | pBBRKmNC903 | 9.59 | 6.66 |
| | | pBBRLKmNC903-PSK::wdh3269 | 12.29 | 10/73 |

Heterologous expression of wax/dgat conferred the capability to recombinant *E. coli* XL1-Blue harbouring pKS: wax/dgat to catalyze the acyl-CoA-dependent acylation of fatty alcohol as well as of DAG (FIG. 2A) at rates similar to those of *A. calcoaceticus* ADP1 (Table 4). These results clearly show that both WS and DGAT activity arise from wax/dgat, which therefore codes for a bifunctional WS/DGAT enzyme. Furthermore, the studies with the knock-out mutant indicate that no other protein exhibiting WS or DGAT activity contributes significantly to wax ester or TAG biosynthesis in *A. calcoaceticus* ADP1. This was supported by the fact that no other wax/dgat homologue could be identified by BLAST (Altschul et al., 1997) search in the preliminary *A. calcoaceticus* ADP1 genome sequence data accessible online at www.genoscope.fr. However, residual trace amounts of TAGs accumulated in the mutants indicate the presence of a minor alternative pathway which is, however, only active at a very low-rate. Functional heterologous expression of wax/dgat was not only demonstrated in *E. coli* S17-1 but also in *Pseudomonas citronellolis* (Table 4).

The bifunctional WS/DGAT comprises 458 amino acids with a theoretical molecular weight of 51.8 kDa and a pI of 9.05. It is a rather amphiphilic protein, and it possesses one putative predicted membrane-spanning region (FIG. 12B).

Figure 13:
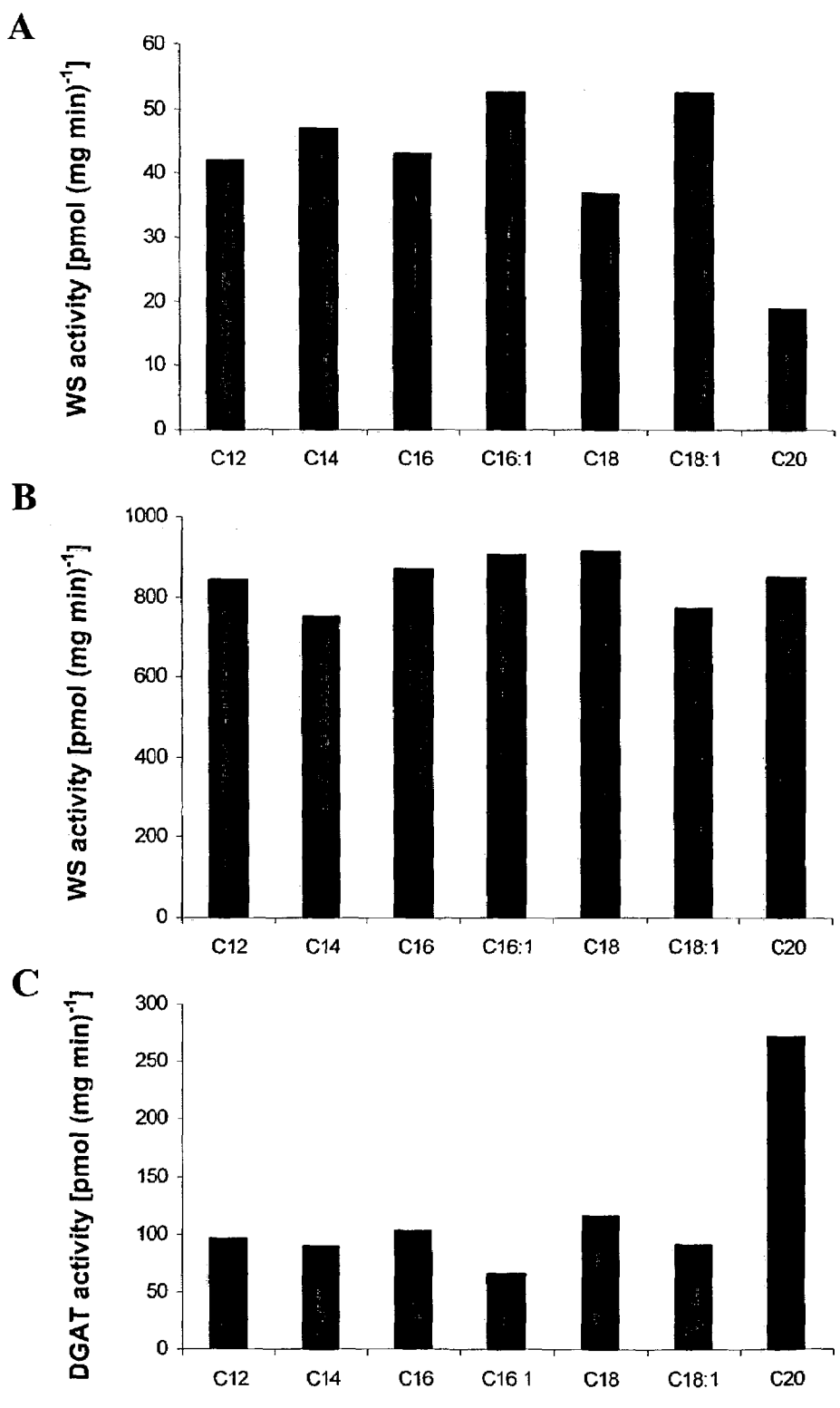
FIGS. 13A, B, C Substrate specificities of the bifunctional WS/DGAT. Measurements were done using insoluble fraction of crude extract of *E. coli* XL1-Blue (pKS::wax/dgat) obtained after 30 min centrifugation at 35,000×g. Values are averages of two independent studies.
(FIG. 13B) Acyl-CoA specificity of the WS reaction.
(FIG. 13C) Acyl-CoA specificity of the DGAT reaction.

Heterologous functional expression of the wax/dgat gene in the alkane-degrading bacterium *P. citronellolis* resulted in an active enzyme which maintained its bifunctionality (Table 4). During cultivation of *P. citronellolis* (pBBR1MCS-2:wax/dgat) under storage conditions, no accumulation of wax esters could be detected by TLC if 0.5% (w/v) gluconate, 0.3% (w/v) 1-hexadecane or 0.3% (w/v) palmitate were used as carbon sources (data not shown). However, cultivation on 0.3% (w/v) 1-hexadecanol, which can serve as a direct substrate for the WS, resulted in recombinant production of wax esters (FIG. 13B). No TAG accumulation could be observed under either conditions.

Example 5

Wax Ester Biosynthesis in *M. smegmatis* mc$^2$155.

Eight WS/DGAT homologous genes could be identified in a preliminary genome sequence of the non-pathogenic strain *M. smegatis* mc$^2$155 (see Table 6), which is publicly accessible online via NCBI. The gene with the highest similarity exhibits 41.0% amino acids identity to WS/DGAT and 67.2% to the hypothetical protein Rv3734c from *M. tuberculosis* H37Rv (Table 5). Recombinant *E. coli* expressing this gene (designated as wdh3269) on plasmid pSK: wdh3269 showed a weak WS and DGAT activity which was slightly but reproducible higher than the vector control (Table 1).

*M. smegmatis* mc$^2$155 cultivated under storage conditions with glucose as sole carbon source exhibited both high WS as well as DGAT activity in vitro (Table 4), but in vivo only TAGs were intracellularly accumulated (FIG. 13A). However, like recombinant *P. citronellolis*, *M. smegatis* mc$^2$155 was also capable of substantial wax ester biosynthesis in vivo when 1-hexadecanol was provided as sole carbon source or as a co-substrate (FIG. 13A).

TABLE 5

Wax/DGAT related proteins in *M. tuberculosis* and *A. thaliana*. Accession numbers correspond to NCBI protein data base. Identities to the *A. calcoaceticus* ADP1 WS/DGAT were based on BLAST search results and calculated for full-length sequences.

| Strain | Protein | Length (amino acids) | Identity (%) | Accession |
|---|---|---|---|---|
| *M. tuberculosis* H37Rv | Rv3740c | 448 | 39.7 | NP__218257 |
| | Rv3734c | 454 | 38.6 | NP__218251 |
| | Rv1425 | 459 | 34.9 | NP__215941 |
| | Rv3480c | 497 | 34.8 | NP__217997 |
| | Rv2285 | 445 | 33.2 | NP__216801 |
| | Rv0895 | 505 | 31.7 | NP__215410 |
| | Rv3088 | 474 | 28.9 | NP__217604 |
| | Rv3130c | 463 | 27.0 | NP__217646 |
| | Rv3087 | 472 | 26.7 | NP__217603 |
| | Rv1760 | 502 | 25.7 | NP__216276 |
| | Rv0221 | 469 | 23.9 | NP__214735 |
| | Rv2484c | 491 | 22.6 | NP__217000 |
| | Rv3371 | 446 | 20.7 | NP__217888 |
| *A. thaliana* | At5g53380 | 483 | 21.3 | NP__200150 |
| | At5g16350 | 488 | 20.5 | NP__197139 |
| | At5g12420 | 480 | 19.8 | NP__568275 |
| | At5g22490 | 482 | 18.9 | NP__197641 |
| | At1g72110 | 479 | 16.5 | NP__177356 |
| | At5g37300 | 481 | 16.0 | NP__568547 |
| | At3g49210 | 518 | 15.6 | NP__190490 |
| | At3g49190 | 522 | 15.5 | NP__190488 |
| | At5g53390 | 485 | 15.1 | NP__200151 |
| | At3g49200 | 507 | 14.4 | NP__190489 |

Example 6

Identification of a Putative Active Site

Figure 10:
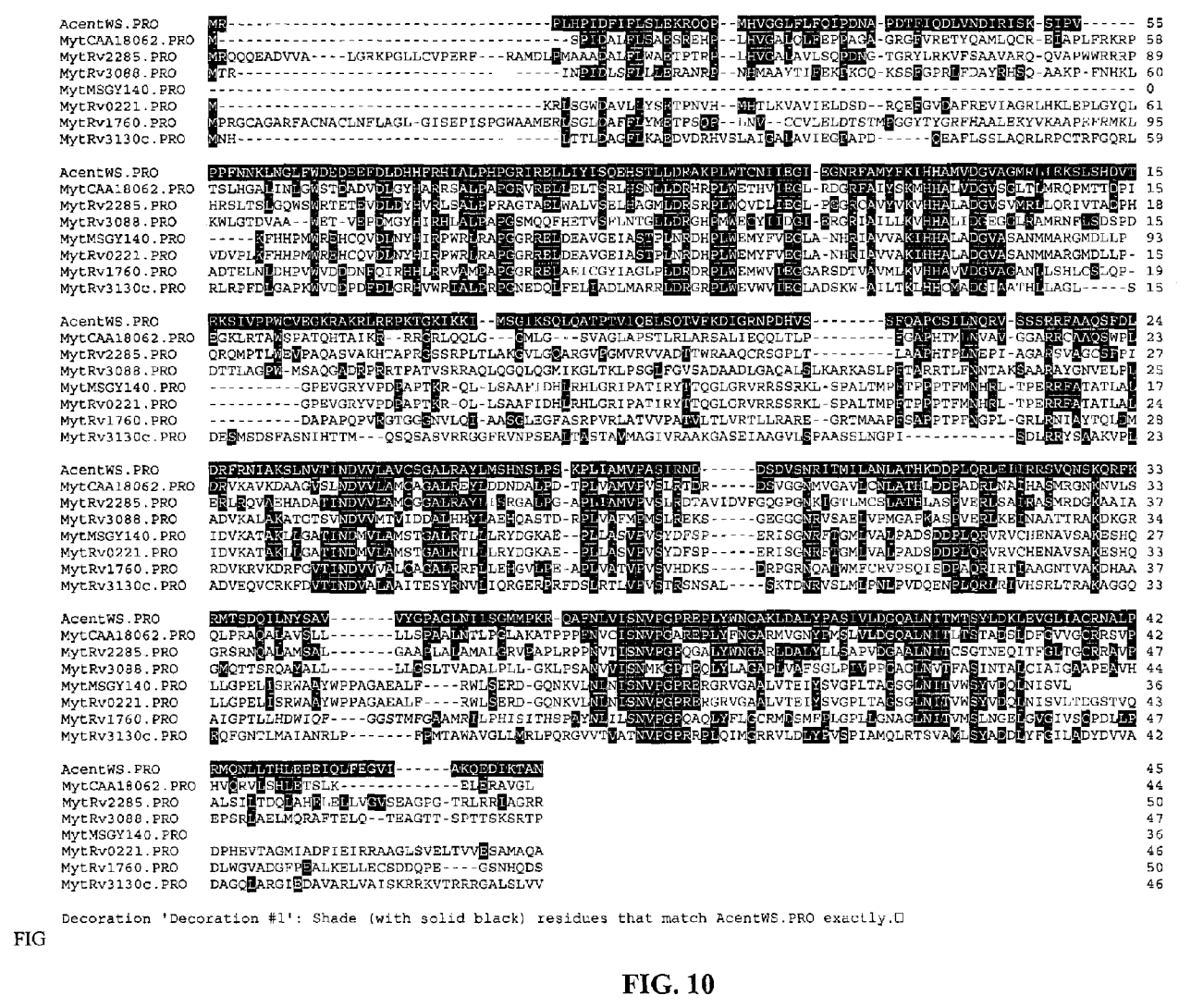

The *A. calcoaceticus* ADP1 WS/DGAT and the related proteins in *Mycobacterium* and *A. thaliana* exhibit in their N-terminal region some partial similarity to a conserved condensing domain found in many multi-domain enzymes synthesizing peptide antibiotics (NCBI Conserved Domain Database accession pfam00668). This condensing domain contains an active-site motif (HHXXXDG), whose second histidine residue is strictly conserved and has been demonstrated to be essential for catalytic activity in nonribosomal peptide bond formation (Stachelhaus et al., 1998). The WS/DGAT and related proteins also contain this putative active site with the motif (HXXXDG) being strictly conserved (FIG. 10). Thus, it is very likely that this site is catalytically participating in the acyl-CoA acyltransferase reactions involved in wax ester and TAG formation (FIG. 12A).

The motif HHXXXDG corresponding to amino acids 132–138 of the *A. calcoaceticus* WS/DGAT is highly conserved, and may be the catalytic site responsible for the ester bond formation (FIG. 10). This motif is the putative active site in the condensing domain found in many multi-domain enzymes synthesising peptide antibiotics.

It was shown that *M. smegatis* mc$^2$155 possesses both DGAT and WS activity in vitro (Table 4), and that this strain can produce TAGs as well as wax esters in vivo (FIG. 13A). Wax ester synthesis from unrelated carbon sources like glucose, however, was hampered probably only by the lacking capability of fatty alcohol biosynthesis. Heterologous expression of the homologue from *M. smegatis* mc$^2$155, which exhibits the highest similarity to the *A. calcoaceticus* ADP1. WS/DGAT (wdh3269), mediated low but significant WS and DGAT activities to recombinant *E. coli* (Table 4); these low activities could result from low expression of the gene. The activities may arise in *M. smegmatis* mc²155 also from WS/DGAT homologues or may be the cumulative result of two or more enzymes. Alternatively to storage lipid synthesis, some of the WS/DGAT homologues could also participate in biosynthesis of cell wall lipids like mycolic acids, which are responsible for the unique properties of the mycobacterial cell wall and can play crucial roles in pathogenesis.

TABLE 6

Distribution of WS/DGAT related proteins in bacteria.

Data were obtained using BLAST search with microbial genomes at NCBI comprising 158 eubacterial + 18 archaeal finished and unfinished genome sequences (as of August 2002). Identities were calculated for full-length sequences.

| Strain | Number of related proteins | Highest identity (%) |
|---|---|---|
| M. tuberculosis CDC1551 | 14 | 39.7 |
| M. tuberculosis H37Rv | 13 | 39.7 |
| M. bovis | 13 | 39.7 |
| M. avium | 10 | 40.4 |
| M. smegmatis mc²155 | 8 | 41.0 |
| M. avium subsp. paratuberculosis | 8 | 40.4 |
| S. coelicolor A3(2) | 2 | 26.6 |
| M. leprae | 1 | 18.9 |

REFERENCES

The following references, to the extent that they provide exemplary procedural or other details supplementary to those set forth herein, are specifically incorporated herein by reference.

U.S. Pat. No. 4,703,004
U.S. Pat. No. 4,782,137
U.S. Pat. No. 4,845,341
U.S. Pat. No. 5,594,115
U.S. Pat. No. 5,935,824
U.S. Pat. No. 6,303,345
Altschul et al., *J. Mol. Biol.*, 215:403–410, 1990.
Altschul et al., *Nucleic Acids Res.*, 25:3389–3402, 1997.
Altschul et al., *Nucleic Acids Res.*, 25:3389–3402, 1997.
Alvarez et al., *Fett/Lipid*, 9:239–246, 1997.
Assaad and Signer, *Molec. General Genet.*, 223:517–520, 1990.
Ausubel et al., In: *Short Protocols in Molecular Biology*, 3Ed., John Wiley & Sons, 1995.
Baptist et al., *Biochem. Biophys. Acta*, 69:400–47, 1963.
Barksdale and Kim, *Mycobacterium. Bacteriol. Rev.*, 41:217–372, 1977.
Bell and Coleman, *Annu. Rev. Biochem.*, 49:459–487, 1980.
Bimboim and Doly, *Nucleic Acids Res.*, 7:1513–1523, 1979.
*Biocomputing. Informatics and Genome Projects*, Smith (Ed.), Academic Press, NY, 1993.
Birren et al., *Genome Analysis*, 1:543–559, 1997.
*BLAST Manual*, Altschul et al., NCBI NLM NIH, Bethesda, Md. 20894.
Bouvier-Navéet al., *Eur. J. Biochem.m.*, 267:85–96, 2000.
Bullock, *BioTechniques*, 5:376–379, 1987.
Carillo and Lipman, *J. Applied Math.*, 48:1073, 1988.
Cases et al., *J. Biol. Chem.*,276:38870–38876, 2001.
Cases et al., *Proc. Natl. Acad. Sci. USA*, 95:13018–13023, 1998.
Chen and Farese, *Trends Cardiovasc. Med.*, 10:188–192, 2000.
Cole et al., *Nature*, 393:537–544, 1998a.
Cole et al., *Nature*, 396:190–198, 1998b.
*Computational Molecular Biology*, Lesk (Ed.), Oxford University Press, NY, 1988.
*Computer Analysis of Sequence Data, Part I*, Griffin and Griffin (Eds.), Humana Press, NJ, 1994.
Coulson, *Trends in Biotech.*, 12:76–80, 1994.
Dahlqvist et al., *Proc. Natl. Acad. Sci. USA*, 97:6487–6492, 2000.
Dalhoff and Rehm, *Eur. J. Appl. Microbiol.*, 3:203–211, 1976.
Davis et al., *Basic Methods in Molecular Biology*, 2nd ed., Appleton and Lange, Sec. 6–8, 1994.
Davis et al., In: *Basic Methods in Molecular Biology*, Elsevier Science Publishing, 1986.
Devereux et al., *Nucl. Acids Res.*, 12(1):387, 1984.
Fish et al., *Eur. J. Appl. Microbiol. Biotechnol.*, 14:259–262, 1982.
Fixter et al., *J. Gen. Microbiol.*, 132:3147–3157, 1986.
Friedrich et al., *J. Bacteriol.* 147:198–205, 1981.
Grund et al., *J. Bacteriol.*, 123:546–556, 1975.
Hanahan, *J. Mol. Biol.*, 166:557–580, 1983.
Herrero et al., *J. Bacteriol.*, 172(11):6557–67, 1990.
Herrero et al., *J. Bacteriol.*, 172(11):6557–67, 1990.
Hobbs et al., *FEBS Lett.*, 452:145–149, 1999.
Hohn and Collins, *Gene*, 11:291–298, 1980.
Hohn and Murray, *Proc. Natl. Acad. Sci. USA*, 74:3259–3263, 1977.
Innis et al., *PCR Protocols*, Academic Press, 1990.
Juni and Janik, *Bacteriol.*, 98:281–288, 1969.
Kovach et al., *Gene*, 166:175–176, 1995.
Kyte and Doolittle, *J. Mol. Biol.*, 157:105–132, 1982.
Kyte and Doolittle, *J. Mol. Biol.*, 157:105–132, 1982.
Lassner, *Lipid Technol.*, 9:5–9, 1997.
Lehner and Kuksis, *J. Biol. Chem.*, 268:8781–8786, 1993.
Lehner and Kuksis, *Prog. Lipid Res.*, 35:169–201, 1996.
Macham and Heydeman, *J. Gen. Microbiol.*, 85:77–84, 1974.
Madford, *Anal. Biochem.*, 72:248–254, 1976.
Maliga et al., In: *Methods in Plant Molecular Biology*, Cold Spring Harbor Laboratory Press, NY, 39, 1995.
Marmur, *J. Mol. Biol.*, 1:208–218, 1961.
Meinkoth and Wahl, *Anal. Biochem.*, 138:267–284, 1984.
Miller and Mekalanos, *J. Bacteriol.*, 170:2575–2583, 1988.
Nakagawa et al., *J. Biochem.*, 80:923–928, 1976.
Oelkers et al., *J. Biol. Chem.*, 277:8877–8881, 2002.
Olukoshi and Packter, *Microbiology*, 140:931–943, 1994.
Overhage et al., *Appl. Micrbiol. Biotechnol.*, 52:820–828, 1999.
Palmen et al., *J. Gen. Microbiol.*, 139:295–305, 1993.
Reiser and Somerville, *J. Bacteriol.*, 179:2969–2975, 1997.
Routaboul et al., *Plant Physiol. Biochem.*, 37:831–840, 1999.
Sambrook, et al., Molecular Cloning: A Laboratory Manual, Third Edition, Cold Spring Harbor, N.Y., 2001.
Sanger et al., *Proc. Natl. Acad. Sci. USA*, 74:5463–5467, 1977.
Schlegel et al. *Arch. Mikrobiol.*, 38:209–222, 1961.
Schlegel et al., *Arch. Mikrobiol.*, 38:209–222, 1961.
*Sequence Analysis in Molecular Biology*, von Heinje (Ed.), Academic Press, NY, 1987.
*Sequence Analysis Primer*, Gribskov and Devereux (Eds.), Stockton Press, NY, 1991.
Simon et al., *Bio/Technology*, 1:784–791, 1983.
Stachelhaus et al., *J. Biol. Chem.*, 273:22773–22781, 1998.
Staijen et al., *J. Bacteriol.*, 181(5):1610–1616, 1999.
Steinbütchel, *In Biomaterials*, Byrom, (Ed., ,123–213, MacMillan, London, 1991.

Stobart et al., *Planta*, 203:58–66, 1997.
Strauss et al., *Anal. Biochem.*, 154:353–360, 1986.
van der Linden, *Biochim. Biophys. Acta*, 77:157–159, 1963.
van Eyk and Bartels, *J. Bacteriol.*, 96:706–712, 1968.
Wang et al., *Biochim. Biophys. Acta*, 260:41–48, 1972.
Williams et al., *J. Appl. Bacteriol.*, 50:551–557, 1981.
Wun et al., *Biochim. Biophys. Acta*, 488:454–463, 1977.
Zou et al., *Plant J.*, 19:645–653, 1999.

---

What is claimed is:

1. An isolated polynucleotide encoding the polypeptide of SEQ ID NO:4.

2. An isolated polynucleotide encoding a polypeptide having wax ester synthase/acyl-CoA:diacylglycerol acyltransferase activity, wherein the polynucleotide comprises the nucleotide sequence of SEQ ID NO: 1 or a nucleotide sequence that hybridizes to the complement thereof under conditions of 5×SSC, 50% formamide and 42° C.

3. The isolated polynucleotide of claim 2, wherein the polynucleotide encodes the polypeptide encoded by SEQ ID NO:1.

4. The isolated polynucleotide of claim 2, wherein the polynucleotide is isolated from a bacterium.

5. The isolated polynucleotide of claim 4, wherein the bacterium is a gram negative bacterium.

6. The isolated polynucleotide of claim 5, wherein the bacterium is *Acinetobacter calcoaceticus*.

7. The isolated polynucleotide of claim 2, comprising the nucleic acid sequence of SEQ ID NO:1 or the complement thereof.

8. A recombinant vector comprising an isolated polynucleotide encoding a polypeptide having wax ester synthase activity and having the nucleotide sequence of SEQ ID NO: 1 or a nucleotide sequence that hybridizes thereto under conditions of 5× SSC, 50% formamide and 42° C.

9. The recombinant vector of claim 8 further comprising at least one additional sequence selected from the group consisting of
   (a) a regulatory sequence operatively coupled to the polynucleotide;
   (b) a selection marker operatively coupled to the polynucleotide;
   (c) a marker sequence operatively coupled to the polynucleotide;
   (d) a purification moiety operatively coupled to the polynucleotide;
   (e) a secretion sequence operatively coupled to the polynucleotide; and
   (f) a targeting sequence operatively coupled to the polynucleotide.

10. The recombinant vector of claim 9, wherein the vector comprises a developmentally-regulated, an organelle-specific, a tissue-specific, an inducible, a constitutive or a cell-specific promoter.

11. The recombinant vector of claim 8, wherein the recombinant vector is selected from the group consisting of pKS:waxEB19, pKS:wax, and pKS:wax-His6C.

12. The recombinant vector of claim 8, wherein the polypeptide has wax ester synthase/acyl-CoA:diacylglycerol acyltransferase (WS/DGAT) activity.

13. The recombinant vector of claim 8, wherein the polynucleotide encodes at least one conserved amino acid sequence selected from the group consisting of HHAXVDGV (SEQ ID NO:16), NDVVLA (SEQ ID NO:17), GALRXYL (SEQ ID NO:18), PLXAMVP (SEQ ID NO:19), ISNVPGP (SEQ ID NO:20), and REPLYXNGA (SEQ ID NO:21).

14. A host cell transformed with the recombinant vector of claim 8.

15. The host cell of claim 14, wherein the host cell is selected from the group consisting of a mammalian cell, plant cell, insect cell, yeast cell, fungus cell, and bacterial cell.

16. The host cell of claim 15, wherein the host cell is selected from the group consisting of *E. Coli* and *Pseudomonas citronellolis*.

17. The host cell of claim 14, wherein the host cell expresses a protein encoded by the recombinant vector.

18. The host cell of claim 17, wherein the expressed protein is secreted by the host cell.

19. A method for producing a wax ester comprising culturing a host cell of claim 14 in the presence of at least one substrate of said polypeptide having wax ester synthase activity under conditions permitting expression of the polypeptide having wax ester synthase activity.

20. The method of claim 19, further comprising isolating the wax ester from the host cell or from the medium in which the host cell is cultured.

21. The method of claim 19, wherein the host cell is a bacterial cell.

* * * * *

SEQUENCE LISTING

<160> NUMBER OF SEQ ID NOS: 31

<210> SEQ ID NO 1
<211> LENGTH: 1377
<212> TYPE: DNA
<213> ORGANISM: Acinetobacter calcoaceticus

<400> SEQUENCE: 1

```
atgcgcccat tacatccgat tgattttata ttcctgtcac tagaaaaaag acaacagcct      60
atgcatgtag gtggtttatt tttgtttcag attcctgata cgccccaga caccttttatt    120
caagatctgg tgaatgatat ccggatatca aaatcaatcc ctgttccacc attcaacaat    180
aaactgaatg ggcttttttg ggatgaagat gaagagtttg atttagatca tcattttcgt    240
catattgcac tgcctcatcc tggtcgtatt cgtgaattgc ttatttatat ttcacaagag    300
cacagtacgc tgctagatcg ggcaaagccc ttgtggacct gcaatattat tgaaggaatt    360
gaaggcaatc gttttgccat gtacttcaaa attcaccatg cgatggtcga tggcgttgct    420
ggtatgcggt taattgaaaa atcactctcc catgatgtaa cagaaaaaag tatcgtgcca    480
ccttggtgtg ttgagggaaa acgtgcaaag cgcttaagag aacctaaaac aggtaaaatt    540
aagaaaatca tgtctggtat taagagtcag cttcaggcga cacccacagt cattcaagag    600
ctttctcaga cagtatttaa agatattgga cgtaatcctg atcatgtttc aagctttcag    660
gcgccttgtt ctattttgaa tcagcgtgtg agctcatcgc gacgttttgc agcacagtct    720
tttgacctag atcgttttcg taatattgcc aaatcgttga atgtgaccat taatgatgtt    780
gtactagcgg tatgttctgg tgcattacgt gcgtatttga tgagtcataa tagtttgcct    840
tcaaaaccat taattgccat ggttccagcc tctattcgca atgacgattc agatgtcagc    900
aaccgtatta cgatgattct ggcaaattg gcaacccaca aagatgatcc tttacaacgt    960
cttgaaatta tccgccgtag tgttcaaaac tcaaagcaac gcttcaaacg tatgaccagc   1020
gatcagattc taaattatag tgctgtcgta tatggccctg caggactcaa cataatttct   1080
ggcatgatgc caaaacgcca agccttcaat ctggttattt ccaatgtgcc tggcccaaga   1140
gagccacttt actggaatgg tgccaaactt gatgcactct acccagcttc aattgtatta   1200
gacggtcaag cattgaatat tacaatgacc agttatttag ataaacttga agttggtttg   1260
attgcatgcc gtaatgcatt gccaagaatg cagaatttac tgacacattt agaagaagaa   1320
attcaactat ttgaaggcgt aattgcaaag caggaagata ttaaaacagc caattaa     1377
```

<210> SEQ ID NO 2
<211> LENGTH: 1464
<212> TYPE: DNA
<213> ORGANISM: Acinetobacter calcoaceticus

<400> SEQUENCE: 2

```
gaattcaagg aggtatccac gctatgcgcc cattacatcc gattgatttt atattcctgt      60
cactagaaaa aagacaacag cctatgcatg taggtggttt atttttgttt cagattcctg    120
ataacgcccc agacaccttt attcaagatc tggtgaatga tatccggata tcaaaatcaa    180
tccctgttcc accattcaac aataaactga atgggctttt ttgggatgaa gatgaagagt    240
```

-continued

```
ttgatttaga tcatcatttt cgtcatattg cactgcctca tcctggtcgt attcgtgaat    300
tgcttattta tatttcacaa gagcacagta cgctgctaga tcgggcaaag cccttgtgga    360
cctgcaatat tattgaagga attgaaggca atcgttttgc catgtacttc aaaattcacc    420
atgcgatggt cgatggcgtt gctggtatgc ggttaattga aaaatcactc tcccatgatg    480
taacagaaaa aagtatcgtg ccaccttggt gtgttgaggg aaaacgtgca aagcgcttaa    540
gagaacctaa aacaggtaaa attaagaaaa tcatgtctgg tattaagagt cagcttcagg    600
cgacacccac agtcattcaa gagctttctc agacagtatt taaagatatt ggacgtaatc    660
ctgatcatgt ttcaagcttt caggcgcctt gttctatttt gaatcagcgt gtgagctcat    720
cgcgacgttt tgcagcacag tcttttgacc tagatcgttt tcgtaatatt gccaaatcgt    780
tgaatgtgac cattaatgat gttgtactag cggtatgttc tggtgcatta cgtgcgtatt    840
tgatgagtca taatagtttg ccttcaaaac cattaattgc catggttcca gcctctattc    900
gcaatgacga ttcagatgtc agcaaccgta ttacgatgat tctggcaaat ttggcaaccc    960
acaaagatga tcctttacaa cgtcttgaaa ttatccgccg tagtgttcaa aactcaaagc   1020
aacgcttcaa acgtatgacc agcgatcaga ttctaaatta tagtgctgtc gtatatggcc   1080
ctgcaggact caacataatt tctggcatga tgccaaaacg ccaagccttc aatctggtta   1140
tttccaatgt gcctggccca agagagccac tttactggaa tggtgccaaa cttgatgcac   1200
tctacccagc ttcaattgta ttagacggtc aagcattgaa tattacaatg accagttatt   1260
tagataaact tgaagttggt ttgattgcat gccgtaatgc attgccaaga atgcagaatt   1320
tactgacaca tttagaagaa gaaattcaac tatttgaagg cgtaattgca aagcaggaag   1380
atattaaaac agccaattaa aaacaataaa cttgatttt taatttatca gataaaacta   1440
aagggctaaa ttagccctgg atcc                                          1464
```

<210> SEQ ID NO 3
<211> LENGTH: 1902
<212> TYPE: DNA
<213> ORGANISM: Acinetobacter calcoaceticus

<400> SEQUENCE: 3

```
gaattctggc ctacatgcag gcaacttaaa taaataattt aaaaaaaacc actgttattg     60
cagtggtttt ttttatgtac tcgctattca gtataattcg ttagatttat gttgattaat    120
aacgatatac tcaatactcg gttctataat tctaaaaaca tagctcataa agggttatta    180
atatctttgc agtgaggcaa tccacgctat gcgcccatta catccgattg attttatatt    240
cctgtcacta gaaaaagac aacagcctat gcatgtaggt ggtttatttt tgtttcagat    300
tcctgataac gccccagaca cctttattca agatctggtg aatgatatcc ggatatcaaa    360
atcaatccct gttccaccat tcaacaataa actgaatggg cttttttggg atgaagatga    420
agagtttgat ttagatcatc attttcgtca tattgcactg cctcatcctg tcgtattcg    480 tgaattgctt atttatatttt cacaagagca cagtacgctg ctagatcggg caaagccctt    540
gtggacctgc aatattattg aaggaattga aggcaatcgt tttgccatgt acttcaaaat    600
tcaccatgcg atggtcgatg gcgttgctgg tatgcggtta attgaaaaat cactctccca    660
tgatgtaaca gaaaaagta cgtgccacc ttggtgtgtt gagggaaaac gtgcaaagcg    720
cttaagagaa cctaaaacag gtaaaattaa gaaaatcatg tctggtatta agagtcagct    780
tcaggcgaca cccacagtca ttcaagagct ttctcagaca gtatttaaag atattggacg    840
```

```
taatcctgat catgtttcaa gctttcaggc gccttgttct attttgaatc agcgtgtgag      900
ctcatcgcga cgttttgcag cacagtcttt tgacctagat cgttttcgta atattgccaa      960
atcgttgaat gtgaccatta atgatgttgt actagcggta tgttctggtg cattacgtgc     1020
gtatttgatg agtcataata gtttgccttc aaaaccatta attgccatgg ttccagcctc     1080
tattcgcaat gacgattcag atgtcagcaa ccgtattacg atgattctgg caaatttggc     1140
aacccacaaa gatgatcctt tacaacgtct tgaaattatc cgccgtagtg ttcaaaactc     1200
aaagcaacgc ttcaaacgta tgaccagcga tcagattcta aattatagtg ctgtcgtata     1260
tggccctgca ggactcaaca taatttctgg catgatgcca aaacgccaag ccttcaatct     1320
ggttatttcc aatgtgcctg gcccaagaga gccactttac tggaatggtg ccaaacttga     1380
tgcactctac ccagcttcaa ttgtattaga cggtcaagca ttgaatatta caatgaccag     1440
ttatttagat aaacttgaag ttggtttgat tgcatgccgt aatgcattgc aagaatgca     1500
gaatttactg acacatttag aagaagaaat tcaactattt gaaggcgtaa ttgcaaagca     1560
ggaagatatt aaaacagcca attaaaaaca ataaacttga ttttttaatt tatcagataa     1620
aactaaaggg ctaaattagc cctttagttt taacagtac gacactgttt aagtaattga     1680
tgacacacat gatgaaccat tgcagtcgtg atctggattt ctttaccttg atcattgacc     1740
atataacaag aattggcagt tttgttatca accatatgcg ttgaaccttg agctagtatt     1800
ctttcactta cattcatgcg agataccccg ttatttgcta agactaatat gggagaaaag     1860
tctttggcta tgttgtgtac ctagtattga aaattcggat cc                        1902
```

<210> SEQ ID NO 4
<211> LENGTH: 458
<212> TYPE: PRT
<213> ORGANISM: Acinetobacter calcoaceticus

<400> SEQUENCE: 4

```
Met Arg Pro Leu His Pro Ile Asp Phe Ile Phe Leu Ser Leu Glu Lys
1               5                   10                  15

Arg Gln Gln Pro Met His Val Gly Gly Leu Phe Leu Phe Gln Ile Pro
            20                  25                  30

Asp Asn Ala Pro Asp Thr Phe Ile Gln Asp Leu Val Asn Asp Ile Arg
        35                  40                  45

Ile Ser Lys Ser Ile Pro Val Pro Pro Phe Asn Asn Lys Leu Asn Gly
    50                  55                  60

Leu Phe Trp Asp Glu Asp Glu Phe Asp Leu Asp His His Phe Arg
65                  70                  75                  80

His Ile Ala Leu Pro His Pro Gly Arg Ile Arg Glu Leu Leu Ile Tyr
                85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190
```

```
Ala Thr Pro Thr Val Ile Gln Glu Leu Ser Gln Thr Val Phe Lys Asp
            195                 200                 205

Ile Gly Arg Asn Pro Asp His Val Ser Ser Phe Gln Ala Pro Cys Ser
            210                 215                 220

Ile Leu Asn Gln Arg Val Ser Ser Ser Arg Arg Phe Ala Ala Gln Ser
225                 230                 235                 240

Phe Asp Leu Asp Arg Phe Arg Asn Ile Ala Lys Ser Leu Asn Val Thr
                245                 250                 255

Ile Asn Asp Val Val Leu Ala Val Cys Ser Gly Ala Leu Arg Ala Tyr
            260                 265                 270

Leu Met Ser His Asn Ser Leu Pro Ser Lys Pro Leu Ile Ala Met Val
            275                 280                 285

Pro Ala Ser Ile Arg Asn Asp Ser Asp Val Ser Asn Arg Ile Thr
            290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
                325                 330                 335

Arg Met Thr Ser Asp Gln Ile Leu Asn Tyr Ser Ala Val Val Tyr Gly
            340                 345                 350

Pro Ala Gly Leu Asn Ile Ile Ser Gly Met Met Pro Lys Arg Gln Ala
            355                 360                 365

Phe Asn Leu Val Ile Ser Asn Val Pro Gly Pro Arg Glu Pro Leu Tyr
            370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
            420                 425                 430

Leu Leu Thr His Leu Glu Glu Glu Ile Gln Leu Phe Glu Gly Val Ile
            435                 440                 445

Ala Lys Gln Glu Asp Ile Lys Thr Ala Asn
450                 455

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5
aaagaattct ggcctacatg caggcaactt aa                                    32

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6
tttggatccg aattttcaat actaggtaca ca                                    32
```

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
aaagaattca aggaggtatc cacgctatgc gcccattac                       39

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
tttggatcca gggctaattt agcccttag tt                               32

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
aaagaattca aggaggtatc cacgctatgc gcccattac                       39

<210> SEQ ID NO 10
<211> LENGTH: 53
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
tttggatcct tagtggtggt ggtggtggtg attggctgtt ttaatatctt cct       53

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
aaagaattca aggaggtatc cacgctatgc gcccattac                       39

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
tttggatcca gggctaattt agcccttag tt                               32

<210> SEQ ID NO 13

```
<211> LENGTH: 9
<212> TYPE: DNA
<213> ORGANISM: Acinetobacter calcoaceticus

<400> SEQUENCE: 13 gcgtatgcg                                                                 9

<210> SEQ ID NO 14
<211> LENGTH: 4
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 14 gagg                                                                      4

<210> SEQ ID NO 15
<211> LENGTH: 8
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 15 aaggaggt                                                                  8

<210> SEQ ID NO 16
<211> LENGTH: 8
<212> TYPE: PRT
<213> ORGANISM: Acinetobacter calcoaceticus
<220> FEATURE:
<221> NAME/KEY: MISC_FEATURE
<222> LOCATION: (4)..(4)
<223> OTHER INFORMATION: Xaa= any amino acid

<400> SEQUENCE: 16

His His Ala Xaa Val Asp Gly Val
 1               5

<210> SEQ ID NO 17
<211> LENGTH: 6
<212> TYPE: PRT
<213> ORGANISM: Acinetobacter calcoaceticus

<400> SEQUENCE: 17

Asn Asp Val Val Leu Ala
 1               5

<210> SEQ ID NO 18
<211> LENGTH: 7
<212> TYPE: PRT
<213> ORGANISM: Acinetobacter calcoaceticus
<220> FEATURE:
<221> NAME/KEY: MISC_FEATURE
<222> LOCATION: (5)..(5)
<223> OTHER INFORMATION: Xaa= any amino acid

<400> SEQUENCE: 18

Gly Ala Leu Arg Xaa Tyr Leu
 1               5

<210> SEQ ID NO 19
<211> LENGTH: 7
<212> TYPE: PRT
```

```
<213> ORGANISM: Acinetobacter calcoaceticus
<220> FEATURE:
<221> NAME/KEY: MISC_FEATURE
<222> LOCATION: (3)..(3)
<223> OTHER INFORMATION: Xaa= any amino acid

<400> SEQUENCE: 19

Pro Leu Xaa Ala Met Val Pro
1               5

<210> SEQ ID NO 20
<211> LENGTH: 7
<212> TYPE: PRT
<213> ORGANISM: Acinetobacter calcoaceticus

<400> SEQUENCE: 20

Ile Ser Asn Val Pro Gly Pro
1               5

<210> SEQ ID NO 21
<211> LENGTH: 9
<212> TYPE: PRT
<213> ORGANISM: Acinetobacter calcoaceticus
<220> FEATURE:
<221> NAME/KEY: MISC_FEATURE
<222> LOCATION: (6)..(6)
<223> OTHER INFORMATION: Xaa= any amino acid

<400> SEQUENCE: 21

Arg Glu Pro Leu Tyr Xaa Asn Gly Ala
1               5

<210> SEQ ID NO 22
<211> LENGTH: 482
<212> TYPE: PRT
<213> ORGANISM: Arabidopsis thaliana

<400> SEQUENCE: 22

Met Glu Lys Lys Met Lys Glu Glu Glu Glu Pro Leu Ser Pro Met
1               5                   10                  15

Ala Arg Ala Phe Gln Glu Pro Ser Ile Asp Cys Gly Ile Val Ile Lys
            20                  25                  30

Phe Gly Cys Lys Thr Lys Ile Asn Pro Asp Val Ile Val Asp Ser Leu
        35                  40                  45

Lys Leu Asn Val Phe Lys His Pro Arg Phe Cys Ser Leu Leu Asp Asp
    50                  55                  60

Asp Gly Thr Lys Trp Leu Arg Thr Asp Val Val Asn Val Glu Glu His
65                  70                  75                  80

Val Phe Val Pro Asp Ile Asp Pro Lys Leu Thr Glu Glu Asp Val Glu
                85                  90                  95

Trp Phe Val Glu Asp Tyr Ile Ser Ser Ile Thr Met Ile Pro Leu Asp
                100                 105                 110

Arg Thr Lys Pro Leu Trp Glu Val His Ile Leu Asn Ala Lys Thr Ser
            115                 120                 125

Asp Ala Glu Ala Ile Cys Val Ile Arg Cys His Ala Leu Gly Asp
        130                 135                 140

Gly Val Ser Ile Leu Ser Leu Ile Leu Ala Ser Thr Arg Lys Thr Ser
145                 150                 155                 160

Glu Pro Glu Ala Phe Ser Thr Leu Pro Val Pro Lys Cys Arg Glu Ser
                165                 170                 175

Tyr Asn His Arg Arg Gly Phe Ser Phe Phe Arg Leu Val Leu Val Val
```

-continued

```
               180                 185                 190
Cys Ser Thr Val Arg Leu Ile Trp Asn Thr Leu Val Asp Ser Phe Leu
            195                 200                 205
Cys Met Ala Thr Ile Phe Phe Leu Lys Asp Thr Asp Thr Pro Leu Lys
        210                 215                 220
Gly Lys Pro Gly Ala Ile Lys Lys Phe Ser His Arg Ile Val Ser Leu
225                 230                 235                 240
Asp Asp Ile Lys Leu Ile Lys Asn Ala Met Glu Met Thr Ile Asn Asp
                245                 250                 255
Val Leu Leu Gly Val Thr Glu Ala Ala Leu Thr Arg Tyr Leu His Gln
            260                 265                 270
Ser Tyr Asp Lys Thr Asn Glu Glu Ala Gly Thr Ser Leu Thr Pro Asn
        275                 280                 285
Arg Gln Asp Leu Leu Asp Arg Ile Arg Leu Arg Ser Leu Ile Val Val
    290                 295                 300
Asn Leu Arg Pro Thr Gly Ser Gln Ser Ile Ala Asp Met Met Ala Lys
305                 310                 315                 320
Gly Ser Lys Cys Arg Trp Gly Asn Tyr Ile Ser Val Ile Leu Phe Pro
                325                 330                 335
Phe Thr Ile Ala Leu Gln Ser Asp Pro Leu Val Tyr Leu Ser Asn Val
            340                 345                 350
Lys Ser Met Ile Asp Arg Lys Lys Asn Ser Leu Ile Thr Tyr Ile Ile
        355                 360                 365
Tyr Thr Phe Ser Glu Phe Val Ile Lys Ala Phe Gly Ile Asn Val Ala
    370                 375                 380
Val Ala Phe Gln Arg Lys Ile Met Leu Asn Thr Thr Met Cys Ile Ser
385                 390                 395                 400
Asn Leu Pro Gly Pro Thr Glu Val Ser Phe His Gly His Pro Ile
                405                 410                 415
Ala Tyr Phe Ala Pro Ser Ile Tyr Gly Leu Pro Gln Ala Leu Thr Ile
            420                 425                 430
His Tyr Leu Ser Tyr Ala Asn Lys Met Ile Ile Ser Val Ala Val Asp
        435                 440                 445
Pro Met Ile Ile Asp Ala His Lys Leu Cys Asp Glu Leu Glu Glu Ser
    450                 455                 460
Leu Lys Asn Met Lys Leu Ala Ile Leu Glu Lys Gly Leu Pro Asn His
465                 470                 475                 480
Val Asn

<210> SEQ ID NO 23
<211> LENGTH: 485
<212> TYPE: PRT
<213> ORGANISM: Arabidopsis thaliana

<400> SEQUENCE: 23

Met Gly Glu Asp Lys Lys Thr Ala Arg Glu Thr Val Glu Glu Pro
1               5                   10                  15
Leu Ser Pro Cys Ser Arg Leu Phe Asn Ser Pro Asp Phe Asn Cys Ala
            20                  25                  30
Ile Ile Val Thr Met Gly Ser Lys Val Lys Gly Asp Thr Pro Ala Ile
        35                  40                  45
Ile His Gly Leu Glu His Thr Leu Val Asn His Pro Arg Phe Ser Ser
    50                  55                  60
Ile Leu Met Asn Asn Gly Lys Lys Pro Arg Trp Val Arg Thr Lys Val
```

-continued

```
             65                  70                  75                  80
Lys Val Glu Glu His Val Ile Val Pro Asp Val Pro Asp Ile Glu
                     85                  90                  95
Asn Pro Asp Gln Tyr Leu Glu Asp Tyr Ile Ser Lys Leu Thr Thr Ile
                100                 105                 110
Pro Met Asp Leu Ser Lys Pro Leu Trp Glu Met His Leu Leu Gly Val
                115                 120                 125
Lys Thr Ser Asn Ala Glu Ser Tyr Ala Ile Leu Lys Ile His His Ser
        130                 135                 140
Leu Gly Asp Gly Met Ser Leu Met Ser Leu Leu Leu Ala Cys Thr Arg
145                 150                 155                 160
Lys Thr Ser Asp Pro Glu Ala Leu Pro Thr Val Ala Val His Lys Lys
                        165                 170                 175
Arg Phe Gly Pro Ser Cys Asn Ser Gly Phe Phe Asn Lys Ile Trp Trp
                    180                 185                 190
Leu Phe Val Gly Leu Trp Phe Ile Leu Arg Leu Leu Phe Asn Thr Phe
            195                 200                 205
Val Asp Ile Leu Met Phe Ala Leu Thr Ile Phe Val Leu Arg Asp Thr
        210                 215                 220
Glu Thr Pro Leu Leu Ala Lys Pro Gly Ser Glu Leu Ile Pro Lys Arg
225                 230                 235                 240
Phe Val His Arg Ile Ile Ser Phe Asp Asp Val Lys Leu Val Lys Asn
                    245                 250                 255
Ala Met Lys Met Thr Val Asn Asp Val Leu Leu Gly Val Thr Gln Ala
                260                 265                 270
Gly Leu Ser Arg Tyr Leu Ser Arg Lys Tyr Asp Gln Glu Ala Thr Pro
            275                 280                 285
Lys Ser Lys Glu Ser Met Arg Arg Ile Arg Leu Arg Ser Ala Ile Met
        290                 295                 300
Ile Asn Leu Arg Pro Asn Ala Gly Ile Glu Ala Leu Ala Asp Met Met
305                 310                 315                 320
Ala Lys Lys Ser Lys Cys Arg Trp Gly Asn Leu Phe Gly Tyr Ile Leu
                    325                 330                 335
Leu Pro Phe Ser Val Gly Leu Glu Thr Asp Pro Leu Glu Tyr Val Arg
                340                 345                 350
Gln Ala Lys Ala Thr Ile Asp Arg Lys Lys His Ser Leu Glu Ala Val
            355                 360                 365
Phe Ser Met Ala Phe Phe Lys Leu Ile Leu Lys Val Leu Gly Leu Lys
        370                 375                 380
Ala Ser Val Val Leu Val Arg Lys Val Ile His Ser Thr Thr Leu Ser
385                 390                 395                 400
Phe Ser Asn Val Gly Pro Lys Glu Glu Ile Thr Phe His Gly His
                    405                 410                 415
Pro Leu Asn Tyr Ile Ser Pro Cys Val Phe Gly His Pro His Ala Leu
                420                 425                 430
Thr Leu His Phe Gln Thr Tyr Ala Asn Lys Val Ile Ile Ser Val Thr
            435                 440                 445
Ala Asp Pro Thr Val Ile Pro Asp Pro His Lys Met Cys Asp Asp Leu
        450                 455                 460
Val Glu Ser Leu Lys Met Ile Lys Ala Ala Val Leu Glu Arg Gly Leu
465                 470                 475                 480
Tyr Glu Ile Glu Val
            485
```

<210> SEQ ID NO 24
<211> LENGTH: 448
<212> TYPE: PRT
<213> ORGANISM: Mycobacterium tuberculosis

<400> SEQUENCE: 24

```
Met Ser Pro Ile Asp Ala Leu Phe Leu Ser Ala Glu Ser Arg Glu His
 1               5                  10                  15

Pro Leu His Val Gly Ala Leu Gln Leu Phe Glu Pro Pro Ala Gly Ala
            20                  25                  30

Gly Arg Gly Phe Val Arg Glu Thr Tyr Gln Ala Met Leu Gln Cys Arg
        35                  40                  45

Glu Ile Ala Pro Leu Phe Arg Lys Arg Pro Thr Ser Leu His Gly Ala
    50                  55                  60

Leu Ile Asn Leu Gly Trp Ser Thr Asp Ala Asp Val Asp Leu Gly Tyr
65                  70                  75                  80

His Ala Arg Arg Ser Ala Leu Pro Ala Pro Gly Arg Val Arg Glu Leu
                85                  90                  95

Leu Glu Leu Thr Ser Arg Leu His Ser Asn Leu Leu Asp Arg His Arg
            100                 105                 110

Pro Leu Trp Glu Thr His Val Ile Glu Gly Leu Arg Asp Gly Arg Phe
        115                 120                 125

Ala Ile Tyr Ser Lys Met His His Ala Leu Val Asp Gly Val Ser Gly
    130                 135                 140

Leu Thr Leu Met Arg Gln Pro Met Thr Thr Asp Pro Ile Glu Gly Lys
145                 150                 155                 160

Leu Arg Thr Ala Trp Ser Pro Ala Thr Gln His Thr Ala Ile Lys Arg
                165                 170                 175

Arg Arg Gly Arg Leu Gln Gln Leu Gly Gly Met Leu Gly Ser Val Ala
            180                 185                 190

Gly Leu Ala Pro Ser Thr Leu Arg Leu Ala Arg Ser Ala Leu Ile Glu
        195                 200                 205

Gln Gln Leu Thr Leu Pro Phe Gly Ala Pro His Thr Met Leu Asn Val
    210                 215                 220

Ala Val Gly Gly Ala Arg Arg Cys Ala Ala Gln Ser Trp Pro Leu Asp
225                 230                 235                 240

Arg Val Lys Ala Val Lys Asp Ala Ala Gly Val Ser Leu Asn Asp Val
                245                 250                 255

Val Leu Ala Met Cys Ala Gly Ala Leu Arg Glu Tyr Leu Asp Asp Asn
            260                 265                 270

Asp Ala Leu Pro Asp Thr Pro Leu Val Ala Met Val Pro Val Ser Leu
        275                 280                 285

Arg Thr Asp Arg Asp Ser Val Gly Gly Asn Met Val Gly Ala Val Leu
    290                 295                 300

Cys Asn Leu Ala Thr His Leu Asp Asp Pro Ala Asp Arg Leu Asn Ala
305                 310                 315                 320

Ile His Ala Ser Met Arg Gly Asn Lys Asn Val Leu Ser Gln Leu Pro
                325                 330                 335

Arg Ala Gln Ala Leu Ala Val Ser Leu Leu Leu Ser Pro Ala Ala
            340                 345                 350

Leu Asn Thr Leu Pro Gly Leu Ala Lys Ala Thr Pro Pro Phe Asn
        355                 360                 365

Val Cys Ile Ser Asn Val Pro Gly Ala Arg Glu Pro Leu Tyr Phe Asn
```

```
              370                 375                 380
Gly Ala Arg Met Val Gly Asn Tyr Pro Met Ser Leu Val Leu Asp Gly
385                 390                 395                 400

Gln Ala Leu Asn Ile Thr Leu Thr Ser Thr Ala Asp Ser Leu Asp Phe
                405                 410                 415

Gly Val Val Gly Cys Arg Arg Ser Val Pro His Val Gln Arg Val Leu
                420                 425                 430

Ser His Leu Glu Thr Ser Leu Lys Glu Leu Glu Arg Ala Val Gly Leu
            435                 440                 445

<210> SEQ ID NO 25
<211> LENGTH: 360
<212> TYPE: PRT
<213> ORGANISM: Mycobacterium tuberculosis

<400> SEQUENCE: 25

Lys Phe His His Pro Met Trp Arg Glu His Cys Gln Val Asp Leu Asn
  1               5                  10                  15

Tyr His Ile Arg Pro Trp Arg Leu Arg Ala Pro Gly Gly Arg Arg Glu
                 20                  25                  30

Leu Asp Glu Ala Val Gly Glu Ile Ala Ser Thr Pro Leu Asn Arg Asp
             35                  40                  45

His Pro Leu Trp Glu Met Tyr Phe Val Glu Gly Leu Ala Asn His Arg
         50                  55                  60

Ile Ala Val Val Ala Lys Ile His His Ala Leu Ala Asp Gly Val Ala
 65                  70                  75                  80

Ser Ala Asn Met Met Ala Arg Gly Met Asp Leu Leu Pro Gly Pro Glu
                 85                  90                  95

Val Gly Arg Tyr Val Pro Asp Pro Ala Pro Thr Lys Arg Gln Leu Leu
                100                 105                 110

Ser Ala Ala Phe Ile Asp His Leu Arg His Leu Gly Arg Ile Pro Ala
            115                 120                 125

Thr Ile Arg Tyr Thr Thr Gln Gly Leu Gly Arg Val Arg Arg Ser Ser
130                 135                 140

Arg Lys Leu Ser Pro Ala Leu Thr Met Pro Phe Thr Pro Pro Pro Thr
145                 150                 155                 160

Phe Met Asn His Arg Leu Thr Pro Glu Arg Arg Phe Ala Thr Ala Thr
                165                 170                 175

Leu Ala Leu Ile Asp Val Lys Ala Thr Ala Lys Leu Leu Gly Ala Thr
            180                 185                 190

Ile Asn Asp Met Val Leu Ala Met Ser Thr Gly Ala Leu Arg Thr Leu
        195                 200                 205

Leu Leu Arg Tyr Asp Gly Lys Ala Glu Pro Leu Leu Ala Ser Val Pro
    210                 215                 220

Val Ser Tyr Asp Phe Ser Pro Glu Arg Ile Ser Gly Asn Arg Phe Thr
225                 230                 235                 240

Gly Met Leu Val Ala Leu Pro Ala Asp Ser Asp Pro Leu Gln Arg
                245                 250                 255

Val Arg Val Cys His Glu Asn Ala Val Ser Ala Lys Glu Ser His Gln
                260                 265                 270

Leu Leu Gly Pro Glu Leu Ile Ser Arg Trp Ala Ala Tyr Trp Pro Pro
            275                 280                 285

Ala Gly Ala Glu Ala Leu Phe Arg Trp Leu Ser Glu Arg Asp Gly Gln
        290                 295                 300
```

```
Asn Lys Val Leu Asn Leu Asn Ile Ser Asn Val Pro Gly Pro Arg Glu
305                 310                 315                 320

Arg Gly Arg Val Gly Ala Ala Leu Val Thr Glu Ile Tyr Ser Val Gly
            325                 330                 335

Pro Leu Thr Ala Gly Ser Gly Leu Asn Ile Thr Val Trp Ser Tyr Val
            340                 345                 350

Asp Gln Leu Asn Ile Ser Val Leu
        355                 360

<210> SEQ ID NO 26
<211> LENGTH: 469
<212> TYPE: PRT
<213> ORGANISM: Mycobacterium tuberculosis

<400> SEQUENCE: 26

Met Lys Arg Leu Ser Gly Trp Asp Ala Val Leu Leu Tyr Ser Glu Thr
1               5                   10                  15

Pro Asn Val His Met His Thr Leu Lys Val Ala Val Ile Glu Leu Asp
            20                  25                  30

Ser Asp Arg Gln Glu Phe Gly Val Asp Ala Phe Arg Glu Val Ile Ala
        35                  40                  45

Gly Arg Leu His Lys Leu Glu Pro Leu Gly Tyr Gln Leu Val Asp Val
    50                  55                  60

Pro Leu Lys Phe His His Pro Met Trp Arg Glu His Cys Gln Val Asp
65                  70                  75                  80

Leu Asn Tyr His Ile Arg Pro Trp Arg Leu Arg Ala Pro Gly Gly Arg
                85                  90                  95

Arg Glu Leu Asp Glu Ala Val Gly Glu Ile Ala Ser Thr Pro Leu Asn
            100                 105                 110

Arg Asp His Pro Leu Trp Glu Met Tyr Phe Val Glu Gly Leu Ala Asn
        115                 120                 125

His Arg Ile Ala Val Val Ala Lys Ile His His Ala Leu Ala Asp Gly
    130                 135                 140

Val Ala Ser Ala Asn Met Met Ala Arg Gly Met Asp Leu Leu Pro Gly
145                 150                 155                 160

Pro Glu Val Gly Arg Tyr Val Pro Asp Pro Ala Pro Thr Lys Arg Gln
                165                 170                 175

Leu Leu Ser Ala Ala Phe Ile Asp His Leu Arg His Leu Gly Arg Ile
            180                 185                 190

Pro Ala Thr Ile Arg Tyr Thr Thr Gln Gly Leu Gly Arg Val Arg Arg
        195                 200                 205

Ser Ser Arg Lys Leu Ser Pro Ala Leu Thr Met Pro Phe Thr Pro Pro
    210                 215                 220

Pro Thr Phe Met Asn His Arg Leu Thr Pro Glu Arg Arg Phe Ala Thr
225                 230                 235                 240

Ala Thr Leu Ala Leu Ile Asp Val Lys Ala Thr Ala Lys Leu Leu Gly
                245                 250                 255

Ala Thr Ile Asn Asp Met Val Leu Ala Met Ser Thr Gly Ala Leu Arg
            260                 265                 270

Thr Leu Leu Leu Arg Tyr Asp Gly Lys Ala Glu Pro Leu Leu Ala Ser
        275                 280                 285

Val Pro Val Ser Tyr Asp Phe Ser Pro Glu Arg Ile Ser Gly Asn Arg
    290                 295                 300

Phe Thr Gly Met Leu Val Ala Leu Pro Ala Asp Ser Asp Pro Leu
305                 310                 315                 320
```

-continued

```
Gln Arg Val Arg Val Cys His Glu Asn Ala Val Ser Ala Lys Glu Ser
            325                 330                 335

His Gln Leu Leu Gly Pro Glu Leu Ile Ser Arg Trp Ala Ala Tyr Trp
            340                 345                 350

Pro Pro Ala Gly Ala Glu Ala Leu Phe Arg Trp Leu Ser Glu Arg Asp
            355                 360                 365

Gly Gln Asn Lys Val Leu Asn Leu Asn Ile Ser Asn Val Pro Gly Pro
            370                 375                 380

Arg Glu Arg Gly Arg Val Gly Ala Ala Leu Val Thr Glu Ile Tyr Ser
385                 390                 395                 400

Val Gly Pro Leu Thr Ala Gly Ser Gly Leu Asn Ile Thr Val Trp Ser
                405                 410                 415

Tyr Val Asp Gln Leu Asn Ile Ser Val Leu Thr Asp Gly Ser Thr Val
            420                 425                 430

Gln Asp Pro His Glu Val Thr Ala Gly Met Ile Ala Asp Phe Ile Glu
            435                 440                 445

Ile Arg Arg Ala Ala Gly Leu Ser Val Glu Leu Thr Val Val Glu Ser
450                 455                 460

Ala Met Ala Gln Ala
465

<210> SEQ ID NO 27
<211> LENGTH: 505
<212> TYPE: PRT
<213> ORGANISM: Mycobacterium tuberculosis

<400> SEQUENCE: 27

Met Arg Gln Gln Gln Glu Ala Asp Val Val Ala Leu Gly Arg Lys Pro
1               5                   10                  15

Gly Leu Leu Cys Val Pro Glu Arg Phe Arg Ala Met Asp Leu Pro Met
                20                  25                  30

Ala Ala Ala Asp Ala Leu Phe Leu Trp Ala Glu Thr Pro Thr Arg Pro
            35                  40                  45

Leu His Val Gly Ala Leu Ala Val Leu Ser Gln Pro Asp Asn Gly Thr
        50                  55                  60

Gly Arg Tyr Leu Arg Lys Val Phe Ser Ala Ala Val Ala Arg Gln Gln
65                  70                  75                  80

Val Ala Pro Trp Trp Arg Arg Pro His Arg Ser Leu Thr Ser Leu
                85                  90                  95

Gly Gln Trp Ser Trp Arg Thr Glu Thr Glu Val Asp Leu Asp Tyr His
                100                 105                 110

Val Arg Leu Ser Ala Leu Pro Pro Arg Ala Gly Thr Ala Glu Leu Trp
            115                 120                 125

Ala Leu Val Ser Glu Leu His Ala Gly Met Leu Asp Arg Ser Arg Pro
        130                 135                 140

Leu Trp Gln Val Asp Leu Ile Glu Gly Leu Pro Gly Gly Arg Cys Ala
145                 150                 155                 160

Val Tyr Val Lys Val His His Ala Leu Ala Asp Gly Val Ser Val Met
                165                 170                 175

Arg Leu Leu Gln Arg Ile Val Thr Ala Asp Pro His Gln Arg Gln Met
                180                 185                 190

Pro Thr Leu Trp Glu Val Pro Ala Gln Ala Ser Val Ala Lys His Thr
            195                 200                 205

Ala Pro Arg Gly Ser Ser Arg Pro Leu Thr Leu Ala Lys Gly Val Leu
```

```
                210                 215                 220
Gly Gln Ala Arg Gly Val Pro Gly Met Val Arg Val Ala Asp Thr
225                 230                 235                 240

Thr Trp Arg Ala Ala Gln Cys Arg Ser Gly Pro Leu Thr Leu Ala Ala
                245                 250                 255

Pro His Thr Pro Leu Asn Glu Pro Ile Ala Gly Ala Arg Ser Val Ala
                260                 265                 270

Gly Cys Ser Phe Pro Ile Glu Arg Leu Arg Gln Val Ala Glu His Ala
                275                 280                 285

Asp Ala Thr Ile Asn Asp Val Val Leu Ala Met Cys Gly Gly Ala Leu
                290                 295                 300

Arg Ala Tyr Leu Ile Ser Arg Gly Ala Leu Pro Gly Ala Pro Leu Ile
305                 310                 315                 320

Ala Met Val Pro Val Ser Leu Arg Asp Thr Ala Val Ile Asp Val Phe
                325                 330                 335

Gly Gln Gly Pro Gly Asn Lys Ile Gly Thr Leu Met Cys Ser Leu Ala
                340                 345                 350

Thr His Leu Ala Ser Pro Val Glu Arg Leu Ser Ala Ile Arg Ala Ser
                355                 360                 365

Met Arg Asp Gly Lys Ala Ala Ile Ala Gly Arg Ser Arg Asn Gln Ala
370                 375                 380

Leu Ala Met Ser Ala Leu Gly Ala Ala Pro Leu Ala Leu Ala Met Ala
385                 390                 395                 400

Leu Gly Arg Val Pro Ala Pro Leu Arg Pro Asn Val Thr Ile Ser
                405                 410                 415

Asn Val Pro Gly Pro Gln Gly Ala Leu Tyr Trp Asn Gly Ala Arg Leu
                420                 425                 430

Asp Ala Leu Tyr Leu Leu Ser Ala Pro Val Asp Gly Ala Ala Leu Asn
                435                 440                 445

Ile Thr Cys Ser Gly Thr Asn Glu Gln Ile Thr Phe Gly Leu Thr Gly
                450                 455                 460

Cys Arg Arg Ala Val Pro Ala Leu Ser Ile Leu Thr Asp Gln Leu Ala
465                 470                 475                 480

His Glu Leu Glu Leu Leu Val Gly Val Ser Glu Ala Gly Pro Gly Thr
                485                 490                 495

Arg Leu Arg Arg Ile Ala Gly Arg Arg
                500                 505

<210> SEQ ID NO 28
<211> LENGTH: 502
<212> TYPE: PRT
<213> ORGANISM: Mycobacterium tuberculosis

<400> SEQUENCE: 28

Met Pro Arg Gly Cys Ala Gly Ala Arg Phe Ala Cys Asn Ala Cys Leu
1               5                   10                  15

Asn Phe Leu Ala Gly Leu Gly Ile Ser Glu Pro Ile Ser Pro Gly Trp
                20                  25                  30

Ala Ala Met Glu Arg Leu Ser Gly Leu Asp Ala Phe Phe Leu Tyr Met
            35                  40                  45

Glu Thr Pro Ser Gln Pro Leu Asn Val Cys Cys Val Leu Glu Leu Asp
        50                  55                  60

Thr Ser Thr Met Pro Gly Gly Tyr Thr Tyr Gly Arg Phe His Ala Ala
65                  70                  75                  80
```

-continued

```
Leu Glu Lys Tyr Val Lys Ala Ala Pro Glu Phe Arg Met Lys Leu Ala
             85                  90                  95
Asp Thr Glu Leu Asn Leu Asp His Pro Val Trp Val Asp Asp Asp Asn
            100                 105                 110
Phe Gln Ile Arg His His Leu Arg Arg Val Ala Met Pro Ala Pro Gly
            115                 120                 125
Gly Arg Arg Glu Leu Ala Glu Ile Cys Gly Tyr Ile Ala Gly Leu Pro
130                 135                 140
Leu Asp Arg Asp Arg Pro Leu Trp Glu Met Trp Val Ile Glu Gly Gly
145                 150                 155                 160
Ala Arg Ser Asp Thr Val Ala Val Met Leu Lys Val His Ala Val
            165                 170                 175
Val Asp Gly Val Ala Gly Ala Asn Leu Leu Ser His Leu Cys Ser Leu
            180                 185                 190
Gln Pro Asp Ala Pro Ala Pro Gln Pro Val Arg Gly Thr Gly Gly Gly
            195                 200                 205
Asn Val Leu Gln Ile Ala Ala Ser Gly Leu Glu Gly Phe Ala Ser Arg
210                 215                 220
Pro Val Arg Leu Ala Thr Val Val Pro Ala Thr Val Leu Thr Leu Val
225                 230                 235                 240
Arg Thr Leu Leu Arg Ala Arg Glu Gly Arg Thr Met Ala Ala Pro Phe
            245                 250                 255
Ser Ala Pro Pro Thr Pro Phe Asn Gly Pro Leu Gly Arg Leu Arg Asn
            260                 265                 270
Ile Ala Tyr Thr Gln Leu Asp Met Arg Asp Val Lys Arg Val Lys Asp
            275                 280                 285
Arg Phe Gly Val Thr Ile Asn Asp Val Val Ala Leu Cys Ala Gly
            290                 295                 300
Ala Leu Arg Arg Phe Leu Leu Glu His Gly Val Leu Pro Glu Ala Pro
305                 310                 315                 320
Leu Val Ala Thr Val Pro Val Ser Val His Asp Lys Ser Asp Arg Pro
            325                 330                 335
Gly Arg Asn Gln Ala Thr Trp Met Phe Cys Arg Val Pro Ser Gln Ile
            340                 345                 350
Ser Asp Pro Ala Gln Arg Ile Arg Thr Ile Ala Ala Gly Asn Thr Val
            355                 360                 365
Ala Lys Asp His Ala Ala Ala Ile Gly Pro Thr Leu Leu His Asp Trp
370                 375                 380
Ile Gln Phe Gly Gly Ser Thr Met Phe Gly Ala Ala Met Arg Ile Leu
385                 390                 395                 400
Pro His Ile Ser Ile Thr His Ser Pro Ala Tyr Asn Leu Ile Leu Ser
            405                 410                 415
Asn Val Pro Gly Pro Gln Ala Gln Leu Tyr Phe Leu Gly Cys Arg Met
            420                 425                 430
Asp Ser Met Phe Pro Leu Gly Pro Leu Leu Gly Asn Ala Gly Leu Asn
            435                 440                 445
Ile Thr Val Met Ser Leu Asn Gly Glu Leu Gly Val Gly Ile Val Ser
            450                 455                 460
Cys Pro Asp Leu Leu Pro Asp Leu Trp Gly Val Ala Asp Gly Phe Pro
465                 470                 475                 480
Glu Ala Leu Lys Glu Leu Leu Glu Cys Ser Asp Asp Gln Pro Glu Gly
            485                 490                 495
Ser Asn His Gln Asp Ser
```

<210> SEQ ID NO 29
<211> LENGTH: 505
<212> TYPE: PRT
<213> ORGANISM: Mycobacterium tuberculosis

<400> SEQUENCE: 29

```
Met Arg Gln Gln Gln Glu Ala Asp Val Val Ala Leu Gly Arg Lys Pro
 1               5                  10                  15
Gly Leu Leu Cys Val Pro Glu Arg Phe Arg Ala Met Asp Leu Pro Met
                20                  25                  30
Ala Ala Ala Asp Ala Leu Phe Leu Trp Ala Glu Thr Pro Thr Arg Pro
            35                  40                  45
Leu His Val Gly Ala Leu Ala Val Leu Ser Gln Pro Asp Asn Gly Thr
        50                  55                  60
Gly Arg Tyr Leu Arg Lys Val Phe Ser Ala Ala Val Ala Arg Gln Gln
 65                  70                  75                  80
Val Ala Pro Trp Trp Arg Arg Pro His Arg Ser Leu Thr Ser Leu
                85                  90                  95
Gly Gln Trp Ser Trp Arg Thr Glu Thr Glu Val Asp Leu Asp Tyr His
                100                 105                 110
Val Arg Leu Ser Ala Leu Pro Pro Arg Ala Gly Thr Ala Glu Leu Trp
            115                 120                 125
Ala Leu Val Ser Glu Leu His Ala Gly Met Leu Asp Arg Ser Arg Pro
        130                 135                 140
Leu Trp Gln Val Asp Leu Ile Glu Gly Leu Pro Gly Gly Arg Cys Ala
145                 150                 155                 160
Val Tyr Val Lys Val His His Ala Leu Ala Asp Gly Val Ser Val Met
                165                 170                 175
Arg Leu Leu Gln Arg Ile Val Thr Ala Asp Pro His Gln Arg Gln Met
                180                 185                 190
Pro Thr Leu Trp Glu Val Pro Ala Gln Ala Ser Val Ala Lys His Thr
            195                 200                 205
Ala Pro Arg Gly Ser Ser Arg Pro Leu Thr Leu Ala Lys Gly Val Leu
        210                 215                 220
Gly Gln Ala Arg Gly Val Pro Gly Met Val Arg Val Ala Asp Thr
225                 230                 235                 240
Thr Trp Arg Ala Ala Gln Cys Arg Ser Gly Pro Leu Thr Leu Ala Ala
                245                 250                 255
Pro His Thr Pro Leu Asn Glu Pro Ile Ala Gly Ala Arg Ser Val Ala
            260                 265                 270
Gly Cys Ser Phe Pro Ile Glu Arg Leu Arg Gln Val Ala Glu His Ala
        275                 280                 285
Asp Ala Thr Ile Asn Asp Val Val Leu Ala Met Cys Gly Gly Ala Leu
    290                 295                 300
Arg Ala Tyr Leu Ile Ser Arg Gly Ala Leu Pro Gly Ala Pro Leu Ile
305                 310                 315                 320
Ala Met Val Pro Val Ser Leu Arg Asp Thr Ala Val Ile Asp Val Phe
                325                 330                 335
Gly Gln Gly Pro Gly Asn Lys Ile Gly Thr Leu Met Cys Ser Leu Ala
            340                 345                 350
Thr His Leu Ala Ser Pro Val Glu Arg Leu Ser Ala Ile Arg Ala Ser
        355                 360                 365
```

```
Met Arg Asp Gly Lys Ala Ala Ile Ala Gly Arg Ser Arg Asn Gln Ala
        370                 375                 380

Leu Ala Met Ser Ala Leu Gly Ala Ala Pro Leu Ala Leu Ala Met Ala
385                 390                 395                 400

Leu Gly Arg Val Pro Ala Pro Leu Arg Pro Asn Val Thr Ile Ser
                405                 410                 415

Asn Val Pro Gly Pro Gln Gly Ala Leu Tyr Trp Asn Gly Ala Arg Leu
            420                 425                 430

Asp Ala Leu Tyr Leu Leu Ser Ala Pro Val Asp Gly Ala Ala Leu Asn
                435                 440                 445

Ile Thr Cys Ser Gly Thr Asn Glu Gln Ile Thr Phe Gly Leu Thr Gly
        450                 455                 460

Cys Arg Arg Ala Val Pro Ala Leu Ser Ile Leu Thr Asp Gln Leu Ala
465                 470                 475                 480

His Glu Leu Glu Leu Leu Val Gly Val Ser Glu Ala Gly Pro Gly Thr
                485                 490                 495

Arg Leu Arg Arg Ile Ala Gly Arg
            500                 505

<210> SEQ ID NO 30
<211> LENGTH: 474
<212> TYPE: PRT
<213> ORGANISM: Mycobacterium tuberculosis

<400> SEQUENCE: 30

Met Thr Arg Ile Asn Pro Ile Asp Leu Ser Phe Leu Leu Leu Glu Arg
  1               5                  10                  15

Ala Asn Arg Pro Asn His Met Ala Ala Tyr Thr Ile Phe Glu Lys Pro
                 20                  25                  30

Lys Gly Gln Lys Ser Ser Phe Gly Pro Arg Leu Phe Asp Ala Tyr Arg
             35                  40                  45

His Ser Gln Ala Ala Lys Pro Phe Asn His Lys Leu Lys Trp Leu Gly
         50                  55                  60

Thr Asp Val Ala Ala Trp Glu Thr Val Glu Pro Asp Met Gly Tyr His
 65                  70                  75                  80

Ile Arg His Leu Ala Leu Pro Ala Pro Gly Ser Met Gln Gln Phe His
                 85                  90                  95

Glu Thr Val Ser Phe Leu Asn Thr Gly Leu Leu Asp Arg Gly His Pro
                100                 105                 110

Met Trp Glu Cys Tyr Ile Ile Asp Gly Ile Glu Arg Gly Arg Ile Ala
            115                 120                 125

Ile Leu Leu Lys Val His His Ala Leu Ile Asp Gly Glu Gly Gly Leu
        130                 135                 140

Arg Ala Met Arg Asn Phe Leu Ser Asp Ser Pro Asp Asp Thr Thr Leu
145                 150                 155                 160

Ala Gly Pro Trp Met Ser Ala Gln Gly Ala Asp Arg Pro Arg Arg Thr
                165                 170                 175

Pro Ala Thr Val Ser Arg Arg Ala Gln Leu Gln Gly Gln Leu Gln Gly
            180                 185                 190

Met Ile Lys Gly Leu Thr Lys Leu Pro Ser Gly Leu Phe Gly Val Ser
        195                 200                 205

Ala Asp Ala Ala Asp Leu Gly Ala Gln Ala Leu Ser Leu Lys Ala Arg
    210                 215                 220

Lys Ala Ser Leu Pro Phe Thr Ala Arg Arg Thr Leu Phe Asn Asn Thr
225                 230                 235                 240
```

-continued

Ala Lys Ser Ala Ala Arg Ala Tyr Gly Asn Val Glu Leu Pro Leu Ala
            245                 250                 255

Asp Val Lys Ala Leu Ala Lys Ala Thr Gly Thr Ser Val Asn Asp Val
        260                 265                 270

Val Met Thr Val Ile Asp Asp Ala Leu His His Tyr Leu Ala Glu His
    275                 280                 285

Gln Ala Ser Thr Asp Arg Pro Leu Val Ala Phe Met Pro Met Ser Leu
290                 295                 300

Arg Glu Lys Ser Gly Glu Gly Gly Asn Arg Val Ser Ala Glu Leu
305                 310                 315                 320

Val Pro Met Gly Ala Pro Lys Ala Ser Pro Val Glu Arg Leu Lys Glu
                325                 330                 335

Ile Asn Ala Ala Thr Thr Arg Ala Lys Asp Lys Gly Arg Gly Met Gln
            340                 345                 350

Thr Thr Ser Arg Gln Ala Tyr Ala Leu Leu Leu Gly Ser Leu Thr
        355                 360                 365

Val Ala Asp Ala Leu Pro Leu Leu Gly Lys Leu Pro Ser Ala Asn Val
    370                 375                 380

Val Ile Ser Asn Met Lys Gly Pro Thr Glu Gln Leu Tyr Leu Ala Gly
385                 390                 395                 400

Ala Pro Leu Val Ala Phe Ser Gly Leu Pro Ile Val Pro Pro Gly Ala
                405                 410                 415

Gly Leu Asn Val Thr Phe Ala Ser Ile Asn Thr Ala Leu Cys Ile Ala
            420                 425                 430

Ile Gly Ala Ala Pro Glu Ala Val His Glu Pro Ser Arg Leu Ala Glu
        435                 440                 445

Leu Met Gln Arg Ala Phe Thr Glu Leu Gln Thr Glu Ala Gly Thr Thr
    450                 455                 460

Ser Pro Thr Thr Ser Lys Ser Arg Thr Pro
465                 470

<210> SEQ ID NO 31
<211> LENGTH: 463
<212> TYPE: PRT
<213> ORGANISM: Mycobacterium tuberculosis

<400> SEQUENCE: 31

Met Asn His Leu Thr Thr Leu Asp Ala Gly Phe Leu Lys Ala Glu Asp
1               5                   10                  15

Val Asp Arg His Val Ser Leu Ala Ile Gly Ala Leu Ala Val Ile Glu
            20                  25                  30

Gly Pro Ala Pro Asp Gln Glu Ala Phe Leu Ser Ser Leu Ala Gln Arg
        35                  40                  45

Leu Arg Pro Cys Thr Arg Phe Gly Gln Arg Leu Arg Leu Arg Pro Phe
    50                  55                  60

Asp Leu Gly Ala Pro Lys Trp Val Asp Pro Asp Phe Asp Leu Gly
65                  70                  75                  80

Arg His Val Trp Arg Ile Ala Leu Pro Arg Pro Gly Asn Glu Asp Gln
                85                  90                  95

Leu Phe Glu Leu Ile Ala Asp Leu Met Ala Arg Arg Leu Asp Arg Gly
            100                 105                 110

Arg Pro Leu Trp Glu Val Trp Val Ile Glu Gly Leu Ala Asp Ser Lys
        115                 120                 125

Trp Ala Ile Leu Thr Lys Leu His His Cys Met Ala Asp Gly Ile Ala

-continued

```
            130                 135                 140
Ala Thr His Leu Leu Ala Gly Leu Ser Asp Glu Ser Met Ser Asp Ser
145                 150                 155                 160

Phe Ala Ser Asn Ile His Thr Thr Met Gln Ser Gln Ser Ala Ser Val
                165                 170                 175

Arg Arg Gly Gly Phe Arg Val Asn Pro Ser Glu Ala Leu Thr Ala Ser
                180                 185                 190

Thr Ala Val Met Ala Gly Ile Val Arg Ala Ala Lys Gly Ala Ser Glu
                195                 200                 205

Ile Ala Ala Gly Val Leu Ser Pro Ala Ala Ser Ser Leu Asn Gly Pro
210                 215                 220

Ile Ser Asp Leu Arg Arg Tyr Ser Ala Ala Lys Val Pro Leu Ala Asp
225                 230                 235                 240

Val Glu Gln Val Cys Arg Lys Phe Asp Val Thr Ile Asn Asp Val Ala
                245                 250                 255

Leu Ala Ala Ile Thr Glu Ser Tyr Arg Asn Val Leu Ile Gln Arg Gly
                260                 265                 270

Glu Arg Pro Arg Phe Asp Ser Leu Arg Thr Leu Val Pro Val Ser Thr
                275                 280                 285

Arg Ser Asn Ser Ala Leu Ser Lys Thr Asp Asn Arg Val Ser Leu Met
290                 295                 300

Leu Pro Asn Leu Pro Val Asp Gln Glu Asn Pro Leu Gln Arg Leu Arg
305                 310                 315                 320

Ile Val His Ser Arg Leu Thr Arg Ala Lys Ala Gly Gly Gln Arg Gln
                325                 330                 335

Phe Gly Asn Thr Leu Met Ala Ile Ala Asn Arg Leu Pro Phe Pro Met
                340                 345                 350

Thr Ala Trp Ala Val Gly Leu Leu Met Arg Leu Pro Gln Arg Gly Val
                355                 360                 365

Val Thr Val Ala Thr Asn Val Pro Gly Pro Arg Arg Pro Leu Gln Ile
                370                 375                 380

Met Gly Arg Arg Val Leu Asp Leu Tyr Pro Val Ser Pro Ile Ala Met
385                 390                 395                 400

Gln Leu Arg Thr Ser Val Ala Met Leu Ser Tyr Ala Asp Asp Leu Tyr
                405                 410                 415

Phe Gly Ile Leu Ala Asp Tyr Asp Val Val Ala Asp Ala Gly Gln Leu
                420                 425                 430

Ala Arg Gly Ile Glu Asp Ala Val Ala Arg Leu Val Ala Ile Ser Lys
                435                 440                 445

Arg Arg Lys Val Thr Arg Arg Gly Ala Leu Ser Leu Val Val
450                 455                 460
```